US012747205B2

(12) United States Patent
Ciufolini et al.

(10) Patent No.: US 12,747,205 B2
(45) Date of Patent: Sep. 29, 2026

(54) SULFUR-CONTAINING LIPIDS

(71) Applicant: THE UNIVERSITY OF BRITISH COLUMBIA, Vancouver (CA)

(72) Inventors: Marco Ciufolini, Vancouver (CA); Mai Lam Ferguson, Vancouver (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 484 days.

(21) Appl. No.: 18/261,723

(22) PCT Filed: Jan. 12, 2022

(86) PCT No.: PCT/CA2022/050042
§ 371 (c)(1),
(2) Date: Jul. 17, 2023

(87) PCT Pub. No.: WO2022/155728
PCT Pub. Date: Jul. 28, 2022

(65) Prior Publication Data

US 2024/0116862 A1 Apr. 11, 2024

Related U.S. Application Data

(60) Provisional application No. 63/139,014, filed on Jan. 19, 2021.

(51) Int. Cl.

| | |
|---|---|
| ***C07C 323/25*** | (2006.01) |
| ***A61K 9/1272*** | (2025.01) |
| ***C12N 15/88*** | (2006.01) |

(52) U.S. Cl.
CPC .......... *C07C 323/25* (2013.01); *A61K 9/1272* (2013.01); *C12N 15/88* (2013.01)

(58) Field of Classification Search
CPC ..... A61K 9/1272; C12N 15/18; C07C 323/25
See application file for complete search history.

(56) References Cited

FOREIGN PATENT DOCUMENTS

| | | | |
|---|---|---|---|
| CA | 3 114 435 | A1 | 4/2020 |
| WO | 2019232095 | A1 | 12/2019 |
| WO | 2020061284 | A1 | 3/2020 |
| WO | 2020072324 | A1 | 4/2020 |
| WO | 2020227510 | A1 | 11/2020 |
| WO | 2021026647 | A1 | 2/2021 |

OTHER PUBLICATIONS

International Search Report mailed Apr. 26, 2022, issued in corresponding International Application No. PCT/CA2022/050042, filed Jan. 12, 2022, 6 pages.
Written Opinion of the International Searching Authority mailed Apr. 26, 2022, issued in corresponding International Application No. PCT/CA2022/050042, filed Jan. 12, 2022, 7 pages.
Chemical Abstract Registry No. 1882029-79-9, "Ethanamine, N,N-dimethyl-2-[(1-methyl-4-penten-1-yl)thio]-," Chemical Catalog Supplier: Ukrorgsyntez Ltd., Mar. 8, 2016, STN Database, 1 page.
Chemical Abstract Registry No. 1877585-34-6, "Ethanamine, 2-[(1-ethylpropyl)thio]-N, N-dimethyl-," Chemical Catalog Supplier: Ukrorgsyntez Ltd., Mar. 2, 2016, STN Database, 1 page.
Chemical Abstract Registry No. 1874589-10-2, "Ethanamine, 2-[(1,2-dimethylpropyl)thio]-N, N-dimethyl-," Chemical Catalog Supplier: Ukrorgsyntez Ltd., Feb. 26, 2016, STN Database, 1 page.
Chemical Abstract Registry No. 1872508-24-1, "Ethanamine, 2-[(1-ethylbutyl)thio]-N, N-dimethyl-," Chemical Catalog Supplier: Ukrorgsyntez Ltd., Feb. 24, 2016, STN Database, 1 page.
Chemical Abstract Registry No. 1871870-82-4, "Ethanamine, N,N-dimethyl-2-[(1-methyl-5-hexen-1-yl)thio]-," Chemical Catalog Supplier: Ukrorgsyntez Ltd., Feb. 22, 2016, STN Database, 1 page.
Chemical Abstract Registry No. 1869777-75-2, "Ethanamine, N,N-dimethyl-2-[(1-methylbutyl)thio]-," Chemical Catalog Supplier: Ukrorgsyntez Ltd., Feb. 18, 2016, STN Database, 1 page.
Extended European Search Report mailed Dec. 13, 2024, issued in corresponding European Application No. 22741969.4, filed Jan. 12, 2022, 11 pages.
Semple, S.C., et al., "Rational design of cationic lipids for siRNA delivery," Nature Biotechnology, vol. 28(2), Feb. 2010, 172-178.
Chen, S., et al., "Influence of particle size on the in vivo potency of lipid nanoparticle formulations of siRNA," Journal of Controlled Release 235 (2016), 236-244.
Kulkarni, J.A., et al., "Fusion-dependent formation of lipid nanoparticles containing macromolecular payloads," Nanoscale, 2019, 11, 9023-9031.
Kulkarni, J.A., et al., "On the Formation and Morphology of Lipid Nanoparticles Containing Ionizable Cationic Lipids and siRNA," ACS Nano 2018, 12, 4787-4795.

*Primary Examiner* — Paul V Ward
(74) *Attorney, Agent, or Firm* — Lamson IP

(57) ABSTRACT

Provided herein is a compound having a structure of Formula (I): (Formula (I)) wherein: D is S, O or an ester; p is 1 to 6; $L_1$ and/or $L_2$ are independently linear or branched $C_1$-$C_{30}$ alkyl, optionally having one or more C═C double bonds of E or Z geometry; and wherein: if D is S then $L_1$ and/or $L_2$ are unsubstituted or substituted with one or more S; and if D is O or an ester, then $L_1$ and/or $L_2$ are substituted with one more S. The compound may be formulated in a lipid nanoparticle for use in the delivery of charged cargo such as nucleic acid. Further provided are methods for making the compound.

(I)

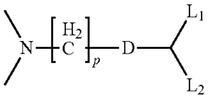

20 Claims, 6 Drawing Sheets

SULFUR-CONTAINING LIPIDS

CROSS REFERENCE TO RELATED APPLICATION

This application is a National Stage of International Application No. PCT/CA2022/050042 filed Jan. 12, 2022, which claims the benefit of U.S. Provisional Patent Application No. 63/139,014 filed Jan. 19, 2021, the disclosure of each of which is expressly incorporated herein by reference in its entirety.

TECHNICAL FIELD

This disclosure relates to a novel lipid containing sulfur for use in lipid nanoparticles, compositions thereof, and methods for their use in the delivery of therapeutic compounds. In particular, the disclosure relates to ionizable lipids containing one or more sulfur atoms. Methods for making and using the sulfur lipids are also provided.

BACKGROUND

Delivery of nucleic acids to target tissues for therapeutic purposes is an important consideration during lipid nanoparticle (LNP) design. Encapsulation of nucleic acids for delivery may allow for lower dosages and reduced side effects. Therapeutic moieties may benefit from selective targeting and improved pharmacokinetic characteristics (i.e., in vivo stability, cellular uptake (for example, lipophilicity), etc.). LNP formulations are the leading systems for in vivo delivery of nucleic acids in clinical applications. Such LNPs incorporate structurally novel ionizable lipids terminating with a tertiary amino group. The present disclosure provides novel sulfur substituted ionizable lipids that may provide for the delivery of nucleic acids.

SUMMARY

This disclosure is based in part on the fortuitous discovery that sulfur modified ionizable lipids can be used to formulate lipid nanoparticles that encapsulate negatively charged cargo, such as nucleic acids.

In accordance with one embodiment, there is provided a compound, the compound having the structure of Formula I:

wherein:

D is selected from the group consisting of S, O, or

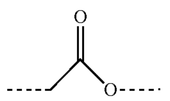

p may be 1 to 6; and $L_1$ and $L_2$ may independently be a linear, branched $C_1$-$C_{30}$ alkyl, optionally having one or more C═C double bonds of E or Z geometry, wherein the $C_1$-$C_{30}$ alkyl may optionally be substituted with one or more S, provided that, when $L_1$ and $L_2$ are both a linear, unsubstituted $C_1$-$C_{30}$ alkyl, having one or more cis or trans C═C double bonds of E or Z geometry, D is S.

In a further embodiment, if D is S then $L_1$ and/or $L_2$ are unsubstituted or substituted with one or more S; and if D is O or an ester, then $L_1$ and/or $L_2$ are substituted with one more S, such as 1 to 4 S atoms.

According to a further embodiment, if D is O or

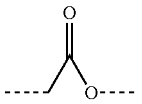

then $L_1$ and/or $L_2$ are substituted with one or more S and the

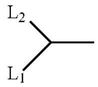

moiety of Formula I has the structure:

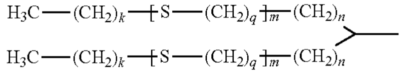

wherein n are independently 1 to 8;

m are independently one or more, such as between 1 and 5;

q are independently 1 to 8; and k is 1 to 8.

wherein n are independently 1 to 8;

m are independently one or more, such as between 1 and 5;

q are independently 1 to 8; and k is 1 to 8.

In accordance with another embodiment, there is provided a compound, the compound having the structure of Formula II:

Formula II

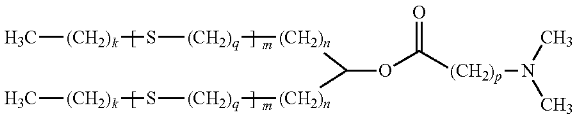

wherein p may be 1 to 6;

q may independently be 1 to 8;

n may independently be 1 to 8;

m may be independently one or more, such as 1 to 5; and k may be 1 to 8.

In accordance with another embodiment, there is provided a compound, the compound having the structure of Formula III:

Formula III

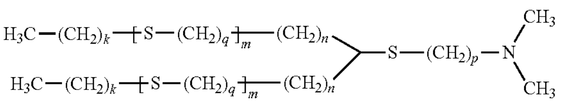

wherein:

p may be 1 to 6;

q may independently be 1 to 8;

n may independently be 1 to 8;

m may independently be 0 to 8 or 0 to 5; and k may independently be 1 to 8.

In accordance with another embodiment there is provided a compound which may be selected from one or more of the following:

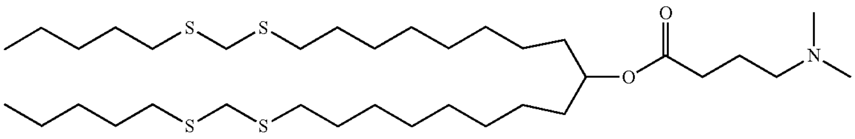

;

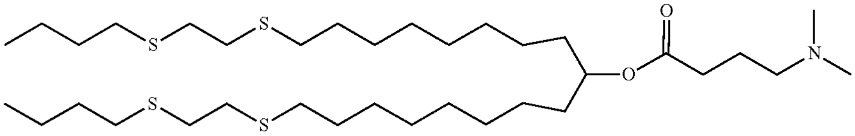

;

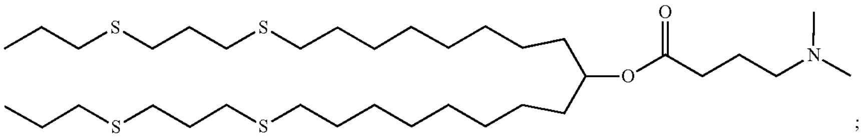

;

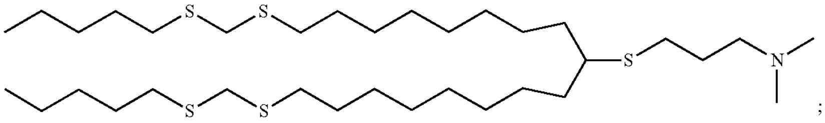

; and

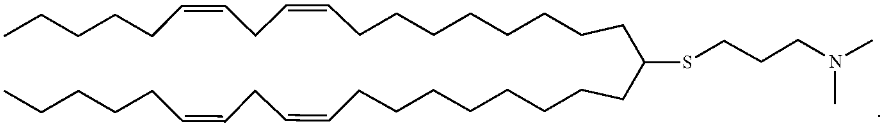

.

In accordance with another embodiment, there is provided a pharmaceutical composition, the pharmaceutical composition comprising a compound described herein and a pharmaceutically acceptable carrier.

In accordance with another embodiment, there is provided a lipid nanoparticle composition, the lipid nanoparticle composition comprising a compound described herein.

In accordance with another embodiment, there is provided a lipid nanoparticle composition, the lipid nanoparticle composition comprising a nucleic acid and a compound described herein.

In accordance with another embodiment, there is provided a compound described herein for encapsulating nucleic acid.

In accordance with another embodiment, there is provided a pharmaceutical composition for encapsulating nucleic acid, comprising compounds described herein and a pharmaceutically acceptable carrier.

In accordance with another embodiment, there is provided a use of a lipid nanoparticle containing one or more compounds described herein for treating, ameliorating, preventing or diagnosing a disease, disorder or condition.

In accordance with another embodiment, there is provided a use of a pharmaceutical composition comprising one or more compounds described herein for treating ameliorating, preventing or diagnosing disease, disorder or condition.

In accordance with another embodiment, there is provided a use of a compound described herein in the manufacture of a medicament.

The compound or composition described herein may be used to treat any indication (e.g., disease, disorder or condition) for which the encapsulated nucleic acid may be used for treatment or prophylactically.

DETAILED DESCRIPTION

Figure 1:
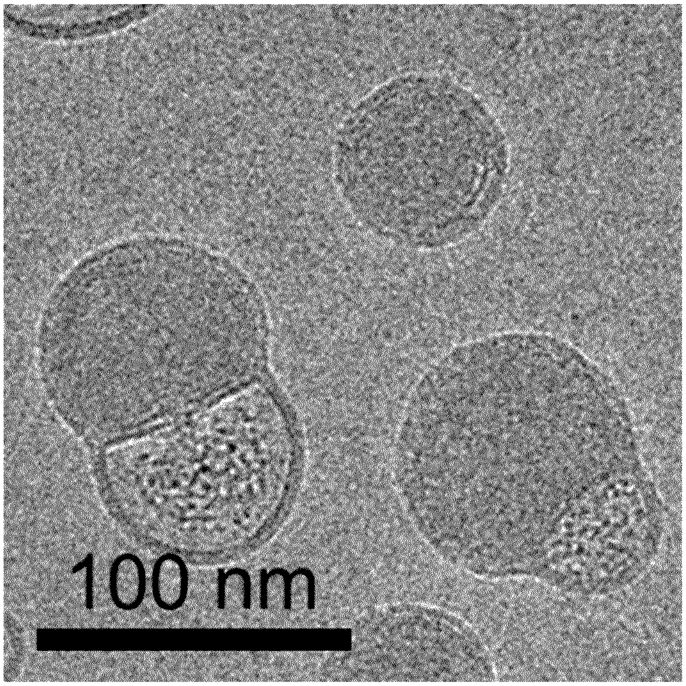
FIG. 1 shows cryogenic transmission electron microscopy (cryo-TEM) analysis of LNP entrapping mRNA. LNPs were composed of compound 13 (MF019)/DSPC/cholesterol/PEG-lipid at molar ratios of 50/10/38.5/1.5.

The ionizable lipids described herein are useful in some embodiments for the formulation in lipid nanoparticles (LNPs) comprising nucleic acid or other negatively charged cargo. Other components included in the lipid nanoparticles may include nucleic acid therapeutics, neutral lipids, cholesterol, and lipids to prevent particle aggregation.

Ionizable Sulfur Lipids

In some non-limiting embodiments, compounds of Table 1 and compounds described herein may be used for encapsulating nucleic acid. In some embodiments, compounds of Table 1 and compounds described herein may be used for encapsulating nucleic acid for treatment, amelioration and/or prevention of at least one indication (e.g., a disease, condition or other ailment) for which the nucleic acid is deemed suitable. In some embodiments, compounds of Table 1 and compounds described herein may be used in the preparation of a medicament or a composition for systemic treatment or localized treatment, prevention or amelioration of an indication (e.g., disease or other condition) described herein.

TABLE 1

Exemplary Sulfur Compounds

| Compound Identifier | Chemical Name | Structure |
|---|---|---|
| Compound 13 (MF019) | 6,8,26,28-tetrathiatritriacontan-17-yl 4-(dimethylamino)butanoate | 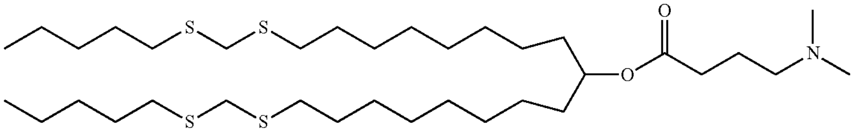 [SMILES: CCCCCSCSCCCCCCCCC(CCCCCCCCSCSCCCCC)OC(=O)CCCN(C)C] |
| Compound 19 | 5,8,26,29-tetrathiatritriacontan-17-yl 4-(dimethylamino)butanoate | 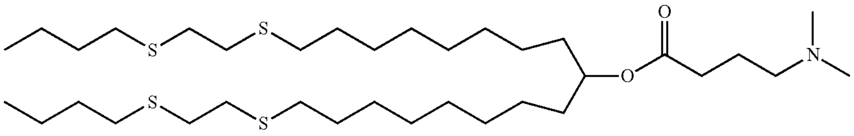 [SMILES: CCCCSCCSCCCCCCCCC(CCCCCCCCSCCSCCCC)OC(=O)CCCN(C)C] |
| Compound 24 | 4,8,26,30-tetrathiatritriacontan-17-yl 4-(dimethylamino)butanoate | 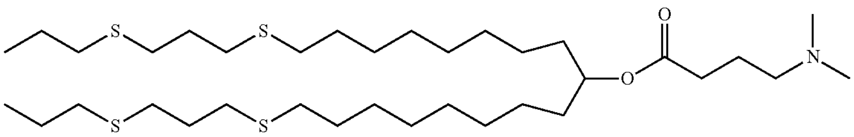 [SMILES: CCCSCCCSCCCCCCCCC(CCCCCCCCSCCCSCCC)OC(=O)CCCN(C)C] |
| Compound 28 | 3-(6,8,26,28-tetrathiatritriacontan-17-ylthio)-N,N-dimethylpropan-1-amine | 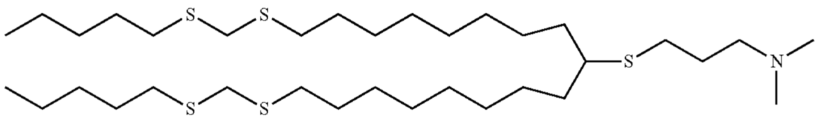 [SMILES: CCCCCSCSCCCCCCCCC(CCCCCCCCSCSCCCCC)SCCCN(C)C] |
| Compound 33 | 3-((6Z,9Z,28Z,31Z)-heptatriaconta-6,9,28,31-tetraen-19-ylthio)-N,N-dimethylpropan-1-amine | 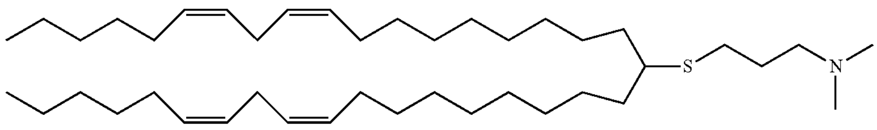 [SMILES: CCCCC/C=C\C/C=C\CCCCCCCCC(CCCCCCCC/C=C\C/C=C\CCCCC)SCCCN(C)C] |

The compounds contemplated in the present disclosure may be described with the general structure of Formula I. shown below, wherein D may represent S, O, or

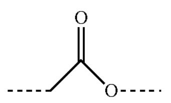

The carbon chain between D and N may be one to six carbons long. The lipid may also incorporate chains of $L_1$ and $L_2$, which may be, independently a linear, branched $C_1$-$C_{30}$ alkyl, optionally having one or more C=C double bonds of E or Z geometry, wherein the $C_1$-$C_{30}$ alkyl may optionally be substituted with one or more S, provided that, when $L_1$ and $L_2$ are both a linear, unsubstituted $C_1$-$C_{30}$ alkyl, having one or more cis or trans C=C double bonds of E or Z geometry, D is S.

Formula I

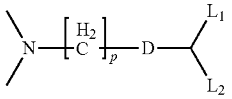

The lipids prepared as described herein may be incorporated into lipid nanoparticles and administered to mammalian subjects (e.g., human patients) for the purpose of treating a disease, illness, or other undesirable physiological condition, which is treatable or curable with the nucleic acid or can prevent such disease, illness, or other undesirable physiological condition.

In some embodiments the lipids described herein, when formulated in a lipid nanoparticle, provide a nucleic acid entrapment above 80% and a pKa range of 6.2-6.8.

In some embodiments the lipids described herein, when formulated in a lipid nanoparticle, provide a nucleic acid entrapment above 90% and a pKa range of 6.3-6.6.

In some embodiments compound 13, when formulated in a lipid nanoparticle, provides a nucleic acid entrapment above 93% and a pKa of 6.41.

As used herein, an ionizable moiety may be any atom or any molecule within a lipid that acquires a negative or positive charge by losing or gaining protons to form ions. Examples of ionizable moieties are —NH, —NHMe, $—NMe_2$, —COOH, —OH, $—NH^+$, $—NH_3^+$, $—NH_2^+$, —SH, etc. The ionizable moiety is most advantageously a tertiary amine group.

In some embodiments, compounds and all different forms thereof (e.g., free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

In some embodiments, compounds may include analogs, isomers, stereoisomers, or related derivatives. Compounds of the present disclosure may include compounds related to the compounds of Table 1 by substitution or replacement of certain substituents with closely related substituents, for instance replacement of an alkyl chain with a related alkyl chain of a different length, and the like.

Lipid Nanoparticles

As noted, the lipids having the structure of any one of Formula I, Formula II or Formula III herein may be incorporated into lipid nanoparticles for the delivery of encapsulated nucleic acid.

It will be understood that the invention is not constrained by the location or the nature of the incorporation of the nucleic acid within the lipid nanoparticle. That is, the term "encapsulated" is not meant to be limited to any specific interaction between the nucleic acid and the lipid nanoparticle. The nucleic acid may be incorporated in the aqueous portion, within any lipid layer or both.

The lipid nanoparticle (LNP) described herein may comprise a helper lipid in addition to the sulfur-containing ionizable lipid. In the context of the present disclosure, the term "helper lipid" includes any vesicle-forming lipid (e.g., bilayer-forming lipid) that may be selected from a phosphatidylcholine lipid, sphingomyelin, or mixtures thereof. In some embodiments, the helper lipid is selected from sphingomyelin, distearoylphosphatidylcholine (DSPC), dioleoylphosphatidylcholine (DOPC), 1-palmitoyl-2-oleoylphosphatidylcholine (POPC) and dipalmitoylphosphatidylcholine (DPPC). In certain embodiments, the helper lipid is DOPC, DSPC or sphingomyelin. In one embodiment, the helper lipid is DSPC. The helper lipid content may include mixtures of two or more different types of different helper lipids.

The phosphatidylcholine content of the lipid nanoparticle in some embodiments is greater than 15 mol %, greater than 20 mol %, greater than 25 mol %, greater than 30 mol %, greater than 32 mol %, greater than 34 mol %, greater than 36 mol %, greater than 38 mol %, greater than 40 mol %, greater than 42 mol %, greater than 44 mol %, greater than 46 mol %, greater than 48 mol % or greater than 50 mol %. In some embodiments, the upper limit of phosphatidylcholine content is 70 mol %, 65 mol %, 60 mol %, 55 mol %, 50 mol % or 45 mol %. The disclosure also encompasses sub-ranges of any combination of the foregoing numerical upper and lower limits.

For example, in certain embodiments, the phosphatidylcholine content is from 20 mol % to 60 mol % or 25 mol % to 60 mol % or 30 mol % to 60 mol % or 35 mol % to 60 mol % or 40 mol % to 60 mol % of total lipid present in the lipid nanoparticle. The phosphatidylcholine lipid content is determined based on the total amount of lipid in the lipid nanoparticle, including the sterol.

In one embodiment, the LNP comprises a sterol, a hydrophilic polymer-lipid conjugate or both.

Examples of sterols include cholesterol, or a cholesterol derivative, such as cholestanol, cholestanone, cholestenone, coprostanol, cholesteryl-2'-hydroxyethyl ether, cholesteryl-4'-hydroxybutyl ether, beta-sitosterol, fucosterol and the like. In one embodiment, the sterol is present at from 15 mol % to 65 mol %, 18 mol % to 50 mol %, 20 mol % to 50 mol %, 25 mol % to 50 mol % or 30 mol % to 50 mol % based on the total lipid present in the lipid nanoparticle. In another embodiment, the sterol is cholesterol and is present at from 15 mol % to 65 mol %, 18 mol % to 50 mol %, 20 mol % to 50 mol %, 25 mol % to 50 mol % or 30 mol % to 50 mol % based on the total lipid and sterol present in the lipid nanoparticle.

In one embodiment, the hydrophilic-polymer lipid conjugate includes (i) a vesicle—forming lipid having a polar head group, and (ii) covalently attached to the head group, a polymer chain that is hydrophilic. Example of hydrophilic polymers include polyethyleneglycol (PEG), polyvinylpyrrolidone, polyvinylmethylether, polyhydroxypropyl methacrylate, polyhydroxypropylmethacrylamide, polyhyd.-oxyethyl acrylate, polymethacrylamide, polydimethylacrylamide, polymethyloxazoline, polyethyloxazoline, polyhydroxyethyloxazoline, polyhydroxypropyloxazoline, polysarcosine and polyaspartamide. In one embodiment, the hydrophilic-polymer lipid conjugate is a PEG-lipid conjugate.

The hydrophilic polymer lipid conjugate may be present in the nanoparticle at 0 mol % to 5 mol %, or at 0.5 mol % to 3 mol %, or at 0.5 mol % to 2.5 mol % or at 0.5 mol % to 2.0 mol % or at 0.5 mol % to 1.8 mol % of total lipid. In another embodiment, the PEG-lipid conjugate is present in the nanoparticle at 0 mol % to 5 mol %, or at 0.5 mol % to 3 mol % or at 0.5 mol % to 2.5 mol % or at 0.5 mol % to 2.0 mol % or at 0.5 mol % to 1.8 mol % of total lipid. In certain embodiments, the PEG-lipid conjugate may be present in the nanoparticle at 0 mol % to 5 mol %, or at 0 mol % to 3 mol %, or at 0 mol % to 2.5 mol % or at 0 mol % to 2.0 mol % or at 0 mol % to 1.8 mol % of total lipid.

Nucleic Acid

LNPs disclosed herein may comprise a "cargo" or "cargo molecule" bearing a net negative or positive charge. This includes but is not limited to any molecule, such as a macromolecule, that is charged at physiological pH. In some non-limiting embodiments, the cargo is a nucleic acid. The nucleic acid may be used in any application, including treating, preventing, ameliorating or diagnosing any disease, disorder or physiological condition.

The nucleic acid includes, without limitation, RNA, including small interfering RNA (siRNA), small nuclear RNA (snRNA), micro RNA (miRNA), messenger RNA (mRNA) or DNA such as vector DNA or linear DNA. The nucleic acid length can vary and can include nucleic acid of 1-50,000 nucleotides in length. The nucleic acid can be in any form, including single stranded DNA or RNA, double stranded DNA or RNA, or hybrids thereof. Single stranded nucleic acid includes antisense oligonucleotides.

In one embodiment, the cargo is an mRNA, which includes a polynucleotide that encodes at least one peptide, polypeptide or protein. The mRNA includes, but is not limited to, small activating RNA (saRNA) and trans-amplifying RNA (taRNA), as described in co-pending U.S. provisional Application No. 63/195,269, titled “mRNA Delivery Using Lipid Nanoparticles”, which is incorporated herein by reference.

The mRNA as used herein encompasses both modified and unmodified mRNA. In one embodiment, the mRNA comprises one or more coding and non-coding regions. The mRNA can be purified from natural sources, produced using recombinant expression systems and optionally purified, or may be chemically synthesized.

In those embodiments in which an mRNA is a chemically synthesized molecule, the mRNA can comprise nucleoside analogs such as analogs having chemically modified bases or sugars, and/or backbone modifications. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, pseudouridine, and 5-methylcytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The mRNAs of the disclosure may be synthesized according to any of a variety of known methods. For example, mRNAs in certain embodiments may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor.

In some embodiments, in vitro synthesized mRNA may be purified before encapsulation to remove undesirable impurities including various enzymes and other reagents used during mRNA synthesis.

The present disclosure may be used to encapsulate mRNAs of a variety of lengths. In some embodiments, the present disclosure may be used to encapsulate in vitro synthesized mRNA ranging from about 1-20 kb, about 1-18 kb, about 1-15 kb, about 1-10 kb, about 5-20 kb, about 5-15 kb, about 5-12 kb, about 5-10 kb, about 8-20 kb, or about 8-15 kb in length.

Typically, mRNA synthesis includes the addition of a “cap” on the 5' end, and a “tail” on the 3' end. The presence of the cap is advantageous in that it may provide resistance to nucleases found in eukaryotic cells. The presence of a “tail” serves to protect the mRNA from exonuclease degradation.

In some embodiments, mRNAs include a 5' and/or 3' untranslated region. In some embodiments, a 5' untranslated region includes one or more elements that affect an mRNA’s stability or translation, for example, an iron responsive element. In some embodiments, a 5' untranslated region may be between about 1 and 500 nucleotides in length or 50 and 500 nucleotides in length or longer.

In some embodiments, a 3' untranslated region includes one or more of a polyadenylation signal, a binding site for proteins that affect an mRNA’s stability of location in a cell, or one or more binding sites for miRNAs. In some embodiments, a 3' untranslated region may be between 1 and 500 nucleotides in length or 50 and 500 nucleotides in length or longer.

While mRNA provided from in vitro transcription reactions may be desirable in certain embodiments, other sources of mRNA are contemplated, such as mRNA produced from bacteria, fungi, plants, and/or animals.

The mRNA sequence may comprise a reporter gene sequence, although the inclusion of a reporter gene sequence in pharmaceutical formulations for administration is optional. Such sequences may be incorporated into mRNA for in vitro studies or for in vivo studies in animal models to assess expression and biodistribution.

In another embodiment, the cargo is an siRNA. An siRNA becomes incorporated into endogenous cellular machineries to result in mRNA breakdown, thereby preventing transcription. Since RNA is easily degraded, its incorporation into a delivery vehicle can reduce or prevent such degradation, thereby facilitating delivery to a target site.

The siRNA encompassed by embodiments of the disclosure may be used to specifically inhibit expression of a wide variety of target polynucleotides. The siRNA molecules targeting specific polynucleotides for any therapeutic, prophylactic or diagnostic application may be readily prepared according to procedures known in the art. An siRNA target site may be selected and corresponding siRNAs may be chemically synthesized, created by in vitro transcription, or expressed from a vector or PCR product. A wide variety of different siRNA molecules may be used to target a specific gene or transcript. The siRNA may be double-stranded RNA, or a hybrid molecule comprising both RNA and DNA, e.g., one RNA strand and one DNA strand. The siRNA may be of a variety of lengths, such as 1 to 30 nucleotides in length or 15 to 30 nucleotides in length or 20 to 25 nucleotides in length. In certain embodiments, the siRNA is double-stranded and has 3' overhangs or 5' overhangs. In certain embodiments, the overhangs are UU or dTdT 3'. In particular embodiments, the siRNA comprises a stem loop structure.

In a further embodiment, the cargo molecule is a microRNA or small nuclear RNA. Micro RNAs (miRNAs) are short, noncoding RNA molecules that are transcribed from genomic DNA, but are not translated into protein. These RNA molecules are believed to play a role in regulation of gene expression by binding to regions of target mRNA. Binding of miRNA to target mRNA may down-regulate gene expression, such as by inducing translational repression, deadenylation or degradation of target mRNA. Small nuclear RNA (snRNA) are typically longer noncoding RNA molecules that are involved in gene splicing. The snRNA molecules may have therapeutic or diagnostic importance in diseases that are an outcome of splicing defects.

In another embodiment, the cargo is a DNA vector. The encapsulated DNA vectors may be administered to a subject for the purpose of repairing, enhancing or blocking or reducing the expression of a cellular protein or peptide. In another embodiment, the encapsulated DNA vectors may be administered to a subject for diagnosis of disease. The DNA vector may localize in target cells (e.g., rapidly dividing cells) and expression of encoded DNA may be used to provide a measurable signal. Accordingly, the nucleotide polymers can be nucleotide sequences including genomic DNA, cDNA, or RNA.

As will be appreciated by those of skill in the art, the vectors may encode promoter regions, operator regions or structural regions. The DNA vectors may contain double-stranded DNA or may be composed of a DNA-RNA hybrid. Non-limiting examples of double-stranded DNA include structural genes, genes including operator control and termination regions, and self-replicating systems such as vector DNA.

Single-stranded nucleic acids include antisense oligonucleotides (complementary to DNA and RNA), ribozymes and triplex-forming oligonucleotides. In order to have prolonged activity, the single-stranded nucleic acids will most advantageously have some or all of the nucleotide linkages substituted with stable, non-phosphodiester linkages, including, for example, phosphorothioate, phosphorodithioate, phophoroselenate, or O-alkyl phosphotriester linkages.

The DNA vectors may include nucleic acids in which modifications have been made in one or more sugar moieties and/or in one or more of the pyrimidine or purine bases. Such sugar modifications may include replacement of one or more hydroxyl groups with halogens, alkyl groups, amines, azido groups or functionalized as ethers or esters. In another embodiment, the entire sugar may be replaced with sterically and electronically similar structures, including aza-sugars and carbocyclic sugar analogs. Modifications in the purine or pyrimidine base moiety include, for example, alkylated purines and pyrimidines, acylated purines or pyrimidines, or other heterocyclic substitutes known to those of skill in the art.

The DNA vector may be modified in certain embodiments with a modifier molecule such as a peptide, protein, steroid or sugar moiety. Modification of a DNA vector with such molecule may facilitate delivery to a target site of interest. In some embodiments, such modification translocates the DNA vector across a nucleus of a target cell. By way of example, a modifier may be able to bind to a specific part of the DNA vector (typically not encoding of the gene-of-interest), but also has a peptide or other modifier that has nucleus-homing effects, such as a nuclear localization signal. A non-limiting example of a modifier is a steroid-peptide nucleic acid conjugate as described by Rebuffat et al., 2002, Faseb J. 16(11):1426-8, which is incorporated herein by reference. The DNA vector may contain sequences encoding different proteins or peptides. Promoter, enhancer, stress or chemically-regulated promoters, antibiotic-sensitive or nutrient-sensitive regions, as well as therapeutic protein encoding sequences, may be included as required. Non-encoding sequences may be present as well in the DNA vector.

The nucleic acids used in the present disclosure can be isolated from natural sources, obtained from such sources as ATCC or GenBank libraries or prepared by synthetic methods. Synthetic nucleic acids can be prepared by a variety of solution or solid phase methods. Generally, solid phase synthesis is preferred. Known procedures for solid phase synthesis of nucleic acids by phosphite-triester, phosphotriester, and H-phosphonate chemistries are widely available.

In one embodiment, the DNA vector is double stranded DNA and comprises more than 700 base pairs, more than 800 base pairs or more than 900 base pairs or more than 1000 base pairs.

In another embodiment, the DNA vector is a nanoplasmid or a minicircle.

Gene editing systems can also be incorporated into delivery vehicles comprising the charged lipid. This includes a Cas9-CRISPR, TALEN and zinc finger nuclease gene editing system. In the case of Cas9-CRISPR, a guide RNA (gRNA), together with a plasmid or mRNA encoding the Cas9 protein may be incorporated into a delivery vehicle comprising the lipids described herein. Optionally, a ribonucleoprotein complex may be incorporated into a delivery vehicle comprising the lipid described herein. Likewise, the disclosure includes embodiments in which genetic material encoding DNA binding and cleavage domains of a zinc finger nuclease or TALEN system are incorporated into a delivery vehicle together with the lipids of the disclosure.

While a variety of nucleic acid cargo molecules are described above, it will be understood that the above examples are non-limiting and the disclosure is not to be considered limiting with respect to the particular cargo molecule encapsulated in the delivery vehicle.

For example, the LNPs described herein may also facilitate the incorporation of proteins and peptides into a delivery vehicle, which includes ribonucleoproteins. This includes both linear and non-linear peptides, proteins or ribonucleoproteins.

Pharmaceutical Formulations

Compounds as described herein may be administered to a subject. As used herein, a "subject" may be a human, non-human primate, rat, mouse, cow, horse, pig, sheep, goat, dog, cat, among other mammals. The subject may be suspected of having or at risk for having an indication for which a therapeutic moiety may provide a benefit.

The treatment may provide a prophylactic (preventive), ameliorative, diagnostic or a therapeutic benefit. The pharmaceutical composition will be administered at any suitable dosage. In one embodiment, the pharmaceutical composition is administered parentally, i.e., intra-arterially, intravenously, subcutaneously or intramuscularly. In yet a further embodiment, the pharmaceutical compositions are for intratumoral or in-utero administration. In another embodiment, the pharmaceutical compositions are administered intranasally, intravitreally, subretinally, intrathecally or via other local routes. The pharmaceutical composition comprises pharmaceutically acceptable salts and/or excipients.

Various alternative embodiments and examples of the invention are described herein. These embodiments and examples are illustrative and should not be construed as limiting the scope of the invention.

EXAMPLES

Materials and Methods (A) Organic Syntheses of Sulfur-Containing Ionizable Lipids General information: Unless otherwise specified, all non-aqueous reactions were performed under an inert argon atmosphere. All glassware was dried with a flame under a stream of argon gas or stored in the oven, and allowed to cool under an inert atmosphere prior to use. Reaction mixture solutions (after aqueous workup) were dried over anhydrous $Na_2SO_4$, filtered, and rotary-evaporated under reduced pressure. Thin-layer chromatography was performed on a alumina plates coated with silica gel (Merck 60 F254 plates) and column chromatography was performed on 230-400 mesh silica gel. Visualization of the developed chromatogram was performed by UV absorbance or staining with ceric ammonium molybdate or potassium permanganate solutions. Nuclear magnetic resonance spectra, $^1H$ (300 MHz) and $^{13}C$ NMR (75 MHz), were recorded at room temperature in $CDCl_3$ solutions. $^1H$ NMR spectra were referenced to $CDCl_3$ (7.26 ppm) and $^{13}C$ NMR spectra were measured in $CDCl_3$ (77.00 ppm), as specified below. Chemical shifts are reported in parts per million (ppm) on the δ scale and coupling constants, J, are in hertz (Hz). Multiplicities are reported as “s” (singlet), “d” (doublet), “dd” (doublet of doublets), “ddd” (doublet of doublets of doublets), “t” (triplet), “q” (quartet), “quin” (quintuplet), “sex” (sextet), “m” (multiplet), and further qualified as “app” (apparent) and “br” (broad). Low- and high-resolution mass spectra (m/z) were obtained in the electrospray (ESI) and field desorption/field ionisation (FD/FI) mode.

Reagents: All reagents and solvents were commercial products and used without further purification except THF (freshly distilled from Na/benzophenone under Ar), $CH_2Cl_2$ (freshly distilled from $CaH_2$ under Ar) and MeOH and EtOH (freshly distilled from Mg under Ar).

(B) Lipid Nanoparticle Preparation and Characterization

Materials: The lipids 1,2-distearoyl-sn-glycero-3-phosphorylcholine (DSPC) and 1,2-distearoyl-sn-glycero-3-phosphoethanolamine-N-[methoxy(polyethylene glycol)-2000] (ammonium salt) (PEG-DMG) were purchased from Avanti Polar Lipids (Alabaster, AL). Cholesterol was purchased from Sigma-Aldrich (St. Louis, MO). The ionizable amino-lipid 2,2-dilinoleyl-4-(2-dimethylaminoethyl)-[1,3]-dioxolane (KC2) was synthesized by Biofine International (Vancouver, BC). Novel sulfur-containing lipids were synthesized as described. TEM grids were purchased from Ted Pella, Inc. (Redding, CA). mRNA encoding firefly luciferase was purchased from TriLink Biotechnologies (San Diego, CA). siRNAs were purchased from Integrated DNA Technologies (IDT—Coralville, IA).

Preparation of LNP Containing mRNA or siRNA

LNP-mRNA systems were prepared as previously described (Kulkarni, J. A. et al. *ACS Nano* 12, 4787-4795 (2018); and Kulkarni, J. A. et al. *Nanoscale* 11, 9023-9031 (2019), each of which is incorporated herein by reference). Briefly, lipid components (ionizable cationic lipid, cholesterol, DSPC, and PEG-lipid) at appropriate ratios were dissolved in ethanol to a concentration of 10 mM total lipid. Luciferase encoding mRNA was dissolved in 25 mM sodium acetate pH 4 buffer to achieve an amine-to-phosphate (N/P) ratio of 6. The two solutions were mixed through a T-junction mixer at a total flow rate of 20 mL/min, and a flow rate ratio of 3:1 v/v (corresponding to 15:5 mL/min aqueous:organic phase). The resulting suspension was subsequently dialyzed against PBS pH 7.4. siRNAs were dissolved in 25 mM sodium acetate pH 4 buffer to achieve an amine-to-phosphate (N/P) ratio of 3. The two solutions were mixed through a T-junction mixer at a total flow rate of 20 mL/min, and a flow rate ratio of 3:1 v/v (corresponding to 15:5 mL/min aqueous:organic phase). The resulting suspension was subsequently dialyzed against PBS pH 7.4.

Cryogenic Transmission Electron Microscopy (Cryo-TEM)

Cryo-TEM was performed as previously described (Kulkarni, J. A. et al. *ACS Nano* 12, 4787-4795 (2018); and Kulkarni, J. A. et al. *Nanoscale* 11, 9023-9031 (2019)). LNP-mRNA systems were concentrated to a final concentration of 20-25 mg/mL of total lipid, deposited onto glow-discharged copper grids, and vitrified using a FEI Mark IV Vitrobot (FEI, Hillsboro, OR). CryoTEM imaging was performed using a 200 kV Glacios microscope equipped with a Falcon III camera.

Analysis of LNPs

The hydrodynamic diameter and size distribution of LNP-mRNA and LNP-siRNA systems were analyzed by dynamic light scattering using a Malvern Zetasizer Nano ZS. Data presented as number-weighted average size. Lipid concentrations were measured using the Cholesterol E Total-Cholesterol assay (Wako Diagnostics, Richmond, VA). RNA concentration and entrapment were measured using the Quant-iT Ribogreen RNA assay as described elsewhere (Kulkarni, J. A. et al. *ACS Nano* 12, 4787-4795 (2018); and Kulkarni, J. A. et al. *Nanoscale* 11, 9023-9031 (2019)).

In Vitro Analysis of Luciferase Expression Using LNP-mRNA Systems

To assess LNP-mRNA efficacy in vitro, HepG2 cells were seeded at 8,000 cells/well in 96-well plates and cultured in DMEM supplemented with 10% FBS. LNP systems entrapping luciferase mRNA were added at various concentrations and luciferase expression was analyzed 24 hours post-treatment using the Steady-Glo Luciferase kit (Promega, Madison, WI).

In Vivo Analysis of Luciferase Expression Using LNP-mRNA Systems

LNP-mRNA were administered intravenously into mice. Animals were euthanized after 4 h, the liver was harvested, homogenized, and suspended in lysis buffer. Luciferase assay was performed using manufacturer's conditions (Promega, Madison, WI). All procedures were approved by the Animal Care Committee at the University of British Columbia and were performed in accordance with guidelines established by the Canadian Council on Animal Care.

In Vitro Analysis of LNP-siRNA Uptake and dGFP Silencing

To assess LNP-siRNA uptake and gene silencing in vitro, H1299-dGFP were seeded at 40,000 cells/well in 24-well plates and cultured in RPMI supplemented with 10% FBS and 1% penicillin/streptomycin. LNP systems entrapping Alexa Fluor 647 modified siRNA (uptake) or siGFP (silencing) were added at various concentrations, cells were detached at indicated time points, washed and analyzed using flow cytometry.

In Vivo Analysis of Factor VII (FVII) Silencing Using LNP-siRNA Systems

FVII knockdown study were performed as previously described.[3] In brief, LNP-siRNA were administered intravenously into WT mice (Charles River Laboratories, Wilmington, MA). Animals were euthanized after 24 h, blood was collected, serum was separated from whole blood using Microtainer Serum Separator tubes (Becton Dickinson, Franklin Lakes, NJ), and the residual serum FVII levels were determined. All procedures were approved by the Animal Care Committee at the University of British Columbia and were performed in accordance with guidelines established by the Canadian Council on Animal Care.

Example 1: Synthesis of the Cationic Ionizable Lipid, 6,8,26,28-tetrathiatritriacontan-17-yl 4-(dimethylamino)butanoate (13)

The synthesis of the cationic ionizable lipid, 6,8,26,28-tetrathiatritriacontan-17-yl 4-(dimethylamino)butanoate (13), also referred to herein as MF019, is show in the Scheme below:

The synthesis of each intermediate in the above scheme is set forth below.

8-((tetrahydro-2H-pyran-2-yl)oxy)octan-1-ol (2)

A mixture of octane-1,8-diol (1.0 g, 6.8 mmol) in dry DCM (5 mL) containing suspended PPTS (0.18 g, 0.70 mmol) was stirred at room temperature for 15 minutes under argon in a dry 25 mL round bottom flask. Neat dihydropyran (0.23 g, 2.76 mmol) was added dropwise over a period of 60 minutes, and the mixture was stirred for 4 h at room temperature. The solvent was removed in vacuo, the residue

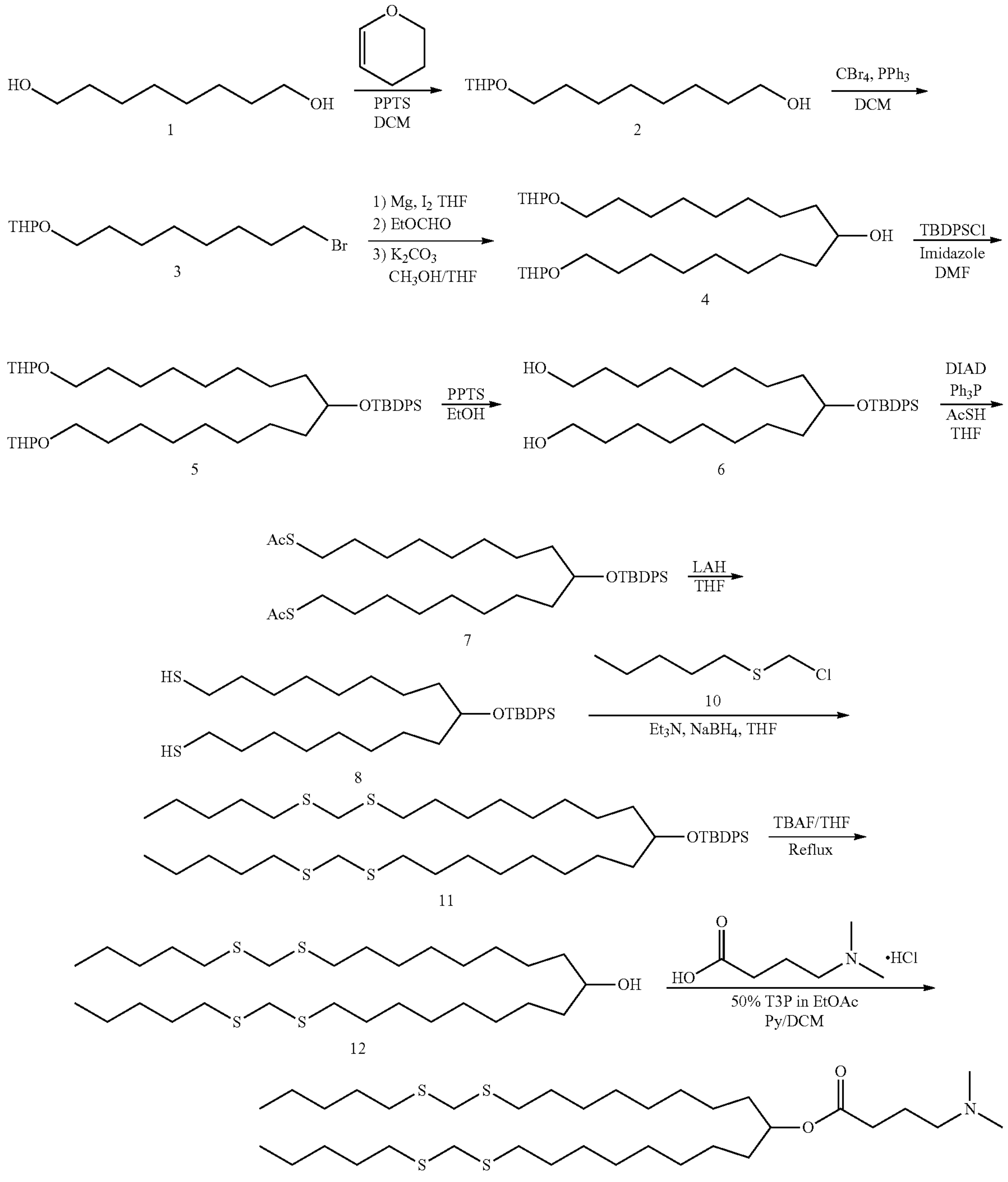

13 was dissolved in $Et_2O$ (10 mL) and the solution was sequentially washed with brine (3×5 mL), dried over $Na_2SO_4$, and evaporated in vacuo. The residue was purified by column chromatography on silica gel (230-400 mesh) eluted with 40% ethyl acetate in hexane. This afforded 0.50 g, 78% of product as colorless oil. $^1H$ NMR: δ 4.59 (t, 1H), 3.89 (m, 1H), 3.75 (m, 1H), 3.66 (t, 2H), 3.52 (m, 1H), 3.40 (m, 1H), 1.84 (m, 1H), 1.73 (m, 1H), 1.58 (m, 8H), 1.35 (br, 9H) ppm. $^{13}C$ NMR: δ 98.9, 67.7, 63.0, 62.4, 32.8, 30.8, 29.7, 29.4, 29.4, 26.2, 25.7, 25.5, 19.7.

2((8-bromooctyl)oxy)tetrahydro-2H-pyran (3)

A solution of 2 (0.5 g, 2.2 mmol) in dry DCM (2 mL) containing suspended $CBr_4$ (0.90 g, 2.72 mmol) was stirred at 0° C. for 10 min under argon in a 10 mL dry round bottom flask. Solid $PPh_3$ (0.85 g, 2.9 mmol) was added to the reaction mixture, and the mixture was stirred vigorously for 5 hours and slowly warmed up from 0° C. to ambient temperature. The solvent was removed in vacuo, the residue was taken up with hexane (5 mL), resulting in a solution of 3 containing a suspended solid. The mixture was filtered through a pad of Celite® and the filtrate was concentrated in vacuo. The residue was purified by column chromatography on silica gel (230-400 mesh) eluted with 4% ethyl acetate in hexane. This afforded 0.39 g (61% yield) of product as colorless oil. $^1H$ NMR: δ 4.59 (t, 1H), 3.89 (m, 1H), 3.75 (m, 1H), 3.52 (m, 1H), 3.42 (t, 2H), 3.41 (m, 1H), 1.87 (m, 3H), 1.58 (m, 6H), 1.35 (br, 9H) ppm. $^{13}C$ NMR: δ 98.9, 67.6, 62.39, 62.4, 34.0, 32.8, 30.8, 29.7, 29.3, 28.7. 28.1, 26.1, 25.5, 19.7.

1,17-bis((tetrahydro-2H-pyran-2-yl)oxy)heptadecan-9-ol (4)

A couple small crystals of $I_2$ were added to a THF (0.5 mL) suspension of Mg turnings (0.055 g, 2.28 mmol) in a dry 5 mL round bottom flask at room temperature. 10-15% of 3 (0.39 g, 1.33 mmol) in THF (1 mL) was added and the mixture was heated at reflux to initiate the reaction (<5 minutes). After initiation, the reaction mixture was removed from the heat and the remainder of the 3 solution was added dropwise over approximately 10 minutes, at which point the reaction mixture had taken on a grey color and a significant portion of the Mg turnings had been consumed. Upon completion of the addition, the reaction mixture was stirred for a further hour. The reaction mixture was chilled in a water bath (10° C.), the ethyl formate (0.046 g, 0.62 mmol) in THF (0.2 mL) was added (<5 minute), then the cold bath was removed and stirring continued at room temperature for 3 hours. The mixture was carefully quenched at room temperature with acetone (1.0 mL), cooled in a water bath and 5 mL of saturated aqueous ammonium chloride solution was added. The reaction mixture was extracted with $Et_2O$ (2×5 mL), the combined organic layers were washed with water (2×5 mL), saturated aqueous sodium chloride solution (2×5 mL). The organic phase was dried over anhydrous sodium sulphate, filtered, and concentrated under reduced pressure. The crude residue was solved in 60% MeOH/THF (2 mL) and $K_2CO_3$ (0.26 g, 1.86 mmol) was added and the resulting mixture stirred at room temperature overnight (14 h). After stirring overnight, the mixture was diluted with $Et_2O$ (4 mL) and suction filtered through a pad of Celite®. The filtrate was washed with saturated aqueous ammonium chloride solution (2×5 mL), saturated aqueous sodium bicarbonate solution (2×5 mL), water (2×5 mL), saturated aqueous sodium chloride solution (2×5 mL), dried over $Na_2SO_4$ and concentrated on a rotary evaporator to afford the crude 4 as a yellow oil. The residue was purified by column chromatography on silica gel (230-400 mesh) eluted with 5% ethyl acetate in hexane. This afforded 0.26 g, 86% of product as a light yellow oil. $^1H$ NMR: δ 4.59 (t, 2H), 3.89 (m, 2H), 3.74 (m, 2H), 3.65 (t, 1H), 3.49 (m, 2H), 3.39 (m, 2H), 1.81 (m, br, 4H), 1.58 (m, 15H), 1.32 (br, 22H) ppm. $^{13}C$ NMR: δ 98.9, 71.9, 67.7, 62.4, 37.5, 30.8, 29.7, 29.65, 29.6, 29.4, 26.2, 25.6, 25.5, 19.7. LRMS: 479.4 [M+Na$^+$]

((1,17-bis((tetrahydro-2H-pyran-2-yl)oxy)heptadecan-9-yl)oxy)(tert-butyl)diphenylsilane (5)

A solution of 4 (0.26 g, 0.57 mmol) in DMF (0.5 mL) was stirred at room temperature under argon in a 5 mL dry round bottom flask. Neat TBDPSCl (0.25 g, 0.91 mmol) was added to the reaction mixture via syringe. Finally, a solution of solid imidazole (0.077 g, 1.14 mmol) in 0.3 mL of DMF was added to the reaction mixture via syringe. The reaction was stirred at room temperature. for 18 hours. Upon the completion of the reaction, 3 mL of DI $H_2O$ was added to the reaction flask and reaction was cooled to 0° C. for 5 minutes. The reaction then was extracted with EtOAc (2×5 mL). The combined organic phased was washed with saturated aqueous sodium bicarbonate solution (2×5 mL), water (2×5 mL), saturated aqueous sodium chloride solution (2×5 mL), dried over $Na_2SO_4$ and concentrated on a rotary evaporator to afford 0.40 g of the crude 5 as a light yellow oil. Crude 5 was used to carry on the next step without purification.

9-((tert-butyldiphenylsilyl)oxy)heptadecane-1,17-diol (6)

A solution of crude 5 (0.40 g, ca. 0.57 mmol) in EtOH (1 mL) in a dry 5 mL round bottom flask was stirred at room temperature under argon. Solid PPTS (0.13 g, 0.51 mmol) was added. The reaction mixture was stirred at 50° C. for 16 hours. Upon the completion of the reaction, 2 mL of brine was added to the mixture, which was then cooled to room temperature and extracted with EtOAc (2×5 mL). The combined extracts were sequentially washed with water (2×5 mL) and saturated aqueous sodium chloride solution (2×5 mL), dried over $Na_2SO_4$ and concentrated on a rotary evaporator to afford crude 6 as a light yellow oil containing a suspended white solid. This material was purified by column chromatography on silica gel (230-400 mesh) by eluting with 30% ethyl acetate in hexane. This afforded 0.22 g, 72% of product as light yellow oil. $^1H$ NMR: δ 7.69 (d, 4H), 7.40 (m, 6H), 4.59 (t, 2H), 3.88 (m, 2H), 3.72 (t, 1H), 3.65 (t, 4H), 1.40 (m, 10H), 1.23 (m, 20H), 1.06 (s, 9H) ppm. $^{13}C$ NMR: δ 135.9, 134.8, 129.35, 127.4, 73.2, 63.1, 36.3, 32.8, 29.6, 29.6, 29.5, 29.3, 27.1, 25.7, 24.8, 19.4.

S,S'-(9-((tert-butyldiphenylsilyl)oxy)heptadecane-1,17-diyl) diethanethioate (7)

Neat DIAD (0.35 g, 1.72 mmol) was added via syringe to a cold (0° C.), stirred solution of $PPh_3$ (0.47 g, 1.8 mmol) in dry THF (1 mL) in a dry 5 mL round bottom flask, under argon. The reaction mixture was stirred at room temperature for 1 hour, during which time a white solid precipitated. The reaction mixture was then cooled in an ice bath, and a solution of 6 (0.22 g, 0.42 mmol) and thioacetic acid (0.13 g, 1.8 mmol) in 0.3 mL of dry THF was added via syringe. Upon completion of the addition (<5 min), the reaction mixture turned clear and took up on orange color. The reaction was stirred at room temperature for 2 hours. Upon the completion of the reaction, the solvent was removed by rotary evaporator. The residue was dissolved in hexanes (5 mL) and filtered through a pad of Celite®. The filtrate was evaporated and the residue was purified by column chromatography on silica gel (230-400 mesh) by eluting with 5% ethyl acetate in hexane. This afforded 0.24 g, 91% of product as yellow oil. $^{1}$H NMR: δ 7.68 (m, 4H), 7.39 (m, 6H), 3.71 (t, 1H), 2.87 (t, 4H), 2.34 (s, 6H), 1.56 (m, 4H), 1.30 (m, 24H), 1.06 (s, 9H) ppm. $^{13}$C NMR: δ 196.0, 135.9, 134.8, 129.4, 127.4, 73.2, 38.9, 36.3, 30.67, 29.6, 29.45, 29.4, 29.2, 29.0, 28.8, 28.4, 27.1, 24.8, 19.4.

9-((tert-butyldiphenylsilyl)oxy)heptadecane-1,17-dithiol (8)

A solution of 7 (0.24 g, 0.37 mmol) in 1 mL of dry THF was added dropwise via syringe to a cold (0° C.), stirred solution of $LiAlH_4$ (0.038 g, 1.0 mmol) in dry THF (1 mL) in a dry 5 mL round bottom flask, under argon. The mixture was allowed to warm to room temperature and stirred at room temperature for 2 hours. Upon the completion of the reaction, the reaction mixture was diluted with 3 mL of $Et_2O$, cooled back to 0° C., sequentially treated with water (38 μL; CAUTION: vigorous reaction, $H_2$ evolution), 15% aqueous NaOH solution (38 μL) and water (115 μL), and then stirred for 15 minutes, during which time it was allowed to warm to room temperature. The solution was filtered, and the solid residue was further washed with $Et_2O$ (2×5 mL). The combined filtrates were concentrated on a rotary evaporator to afford 0.20 g, 96% of the crude 8 as yellow oil. Crude 8 was directly advanced to the next step without purification.

(chloromethyl)(pentyl)sulfane (10)

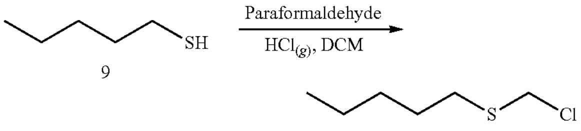

9

10

Gaseous HCl was bubbled through a cold (−15° C., ice/salt bath) solution of 9 (0.23 g, 2.2 mmol) in dry DCM (2 mL) containing suspended paraformaldehyde (0.10 g, 3.3 mmol) and maintained under argon (balloon, needle vent). The mixture was stirred for 2 hours at −15° C. The solvent was removed under reduced pressure and DI $H_2O$ was added to the residue until all the solid dissolved (ca. 5 mL). The mixture was extracted with $Et_2O$ (3×5 mL) and the combined extracts were sequentially washed with saturated aqueous sodium bicarbonate solution (3×5 mL), water (3×5 mL), saturated aqueous sodium chloride solution (2×5 mL), dried over $Na_2SO_4$ and concentrated on a rotary evaporator to afford 0.34 g of 10 (quantitative) as a colorless oil. Compound 10 and related substances are sensitive materials that are best used without further purification. $^{1}$H NMR: δ 4.77 (s, 2H), 2.76 (t, 2H), 1.68 (m, 2H), 1.39 (m, 4H), 0.93 (t, 3H) ppm. $^{13}$C NMR: δ 49.9, 31.6, 30.9, 28.3, 22.2, 13.9.

2,2-dimethyl-5-(8-(((pentylthio)methyl)thio)octyl)-3,3-diphenyl-4-oxa-14,16-dithia-3-silahenicosane (11)

Neat 10 (0.14 g, 0.90 mmol) was added via syringe to a stirred solution of 8 (0.2 g, 0.36 mmol) and $Et_3N$ (0.091 g, 0.90 mmol) in dry THF (1 mL) containing suspended $NaBH_4$ (0.034 g, 0.90 mmol), in a dry 5 mL round bottom flask, under argon. The mixture was heated to reflux for 3 hours. Upon completion of the reaction, the reaction mixture was cooled to 0° C. and diluted with 5 mL of $Et_2O$. Saturated aqueous ammonium chloride solution (4 mL) was added (CAUTION: $H_2$ evolution) and the mixture was extracted with $Et_2O$ (2×5 mL). The combined extracts were sequentially washed with saturated aqueous sodium bicarbonate solution (3×5 mL), saturated aqueous ammonium chloride solution (2×5 mL), and saturated aqueous sodium chloride solution (2×5 mL); dried over anhydrous sodium sulfate, filtered, and concentrated under reduced pressure. The residue was purified by column chromatography on silica gel (230-400 mesh) by eluting with 5% ethyl acetate in hexane. This afforded 0.21 g (73% yield) of product as a white solid. $^{1}$H NMR (300 MHz, $CDCl_3$): δ $^{1}$H NMR: 7.68 (m, 4H), 7.39 (m, 6H), 3.72 (t, 1H), 3.67 (s, 4H), 2.63 (m, 8H), 1.60 (m, 10H), 1.38 (m, 20H), 1.21 (m, 10H), 1.06 (s, 9H), 0.92 (t, 6H) ppm. $^{13}$C NMR: δ 135.9, 134.8, 129.4, 127.4, 73.2, 49.9, 36.3, 35.4, 31.7, 31.1, 30.8, 29.6, 29.4, 29.2, 29.1, 28.9, 28.8, 28.3, 27.1, 24.9, 22.3, 19.4, 14.0.

6,8,26,28-tetrathiatritriacontan-17-ol (12)

A mixture of TBDPS ether 11 (0.21 g, 0.27 mmol) and TBAF (1.0 M in THF, 2.7 mL, 2.7 mmol) was refluxed for 12 h. The solvent was removed under reduced pressure and the residue was dissolved in diethyl ether (5 mL), sequentially washed with saturated aqueous sodium bicarbonate solution (2×5 mL), water (2×5 mL), and saturated aqueous sodium chloride solution (2×5 mL). The organic phase was dried over anhydrous sodium sulfate, filtered through Celite®, and concentrated under reduced pressure. The residue was purified by column chromatography on silica gel (230-400 mesh) by eluting with 10% ethyl acetate in hexane. This afforded 0.11 g of product (71%) as white solid. $^{1}$H NMR (300 MHz, $CDCl_3$): δ 3.68 (s, 4H), 3.60 (m, 1H), 2.64 (m, 8H), 1.61 (m, 10H), 1.31 (m, 30H), 0.92 (t, 6H) ppm. $^{13}$C NMR: δ 72.0, 37.5, 35.4, 31.1, 30.8, 29.6, 29.5, 29.2, 29.1, 28.9, 28.8, 25.7, 22.3, 13.9.

6,8,26,28-tetrathiatritriacontan-17-yl 4-(dimethylamino)butanoate (13)

Propylphosphonic anhydride (T3P, 50% w/w in EtOAc, 0.25 g, 0.40 mmol) was added to a dichloromethane (1 mL) solution of alcohol 12 (0.11 g, 0.20 mmol), pyridine (0.032 g, 0.40 mmol), and the hydrochloride salt of dimethylaminobutyric acid (0.05 g, 0.30 mmol). The reaction mixture was stirred at room temperature overnight, whereupon TLC analysis showed complete disappearance of the starting material. The solvent was removed under reduced pressure and the residue was dissolved in ethyl acetate (5 mL) and sequentially washed with saturated aqueous ammonium chloride solution (2×5 mL), water (2×5 mL), and saturated aqueous sodium chloride solution (2×5 mL). The organic phase was dried over anhydrous sodium sulfate, filtered through Celite®, and concentrated under reduced pressure. The crude product was purified by Flash column chromatography on silica gel (230-400 mesh) by eluting with 5-15% ethyl acetate in 0.5% NEt3 in hexane to afford 0.12 g of product (91%) as a pale yellow oil. $^{1}$H NMR (300 MHz, $CDCl_3$): δ 4.85 (m, 1H), 3.65 (s, 4H), 2.61 (m, 8H), 2.30 (m, 10H), 1.77 (m, 2H), 1.57 (m, 12H), 1.31 (m, 28H), 0.89 (t, 6H) ppm. $^{13}$C NMR: δ 172.09, 75.37, 57.23, 43.07, 35.52, 34.10, 31.18, 31.07, 30.93, 29.53, 29.49, 29.24, 29.14, 28.95, 28.87, 25.45, 22.40. 19.85, 14.09.

Example 2: Synthesis of the Cationic Ionizable Lipid, 5,8,26,29-tetrathiatritriacontan-17-yl 4-(dimethylamino)butanoate (19)

The synthesis of the cationic ionizable lipid, 5,8,26,29-tetrathiatritriacontan-17-yl 4-(dimethylamino)butanoate (19), is shown in the reaction scheme below, followed by a description of the synthesis of each intermediate thereof.

product (75%) as a colorless oil. $^1$H NMR (300 MHz, $CDCl_3$): δ 7.68-7.65 (m, 4H), 7.43-7.35 (m, 6H), 4.21 (t, 4H, J=6.6 Hz), 4.12 (quin, 1H, J=7.2 Hz), 2.99 (s, 6H), 1.76-1.67 (m, 4H), 1.40-1.33 (m, 8H), 1.27-1.14 (m, 16H), 1.04 (s, 9H) ppm. $^{13}$C NMR (300 MHz, $CDCl_3$): δ 135.7, 134.5, 129.2, 127.2, 72.9, 70.1, 36.9, 36.1, 29.2, 29.0, 28.9, 28.7, 26.9, 25.1, 24.6, 19.2.

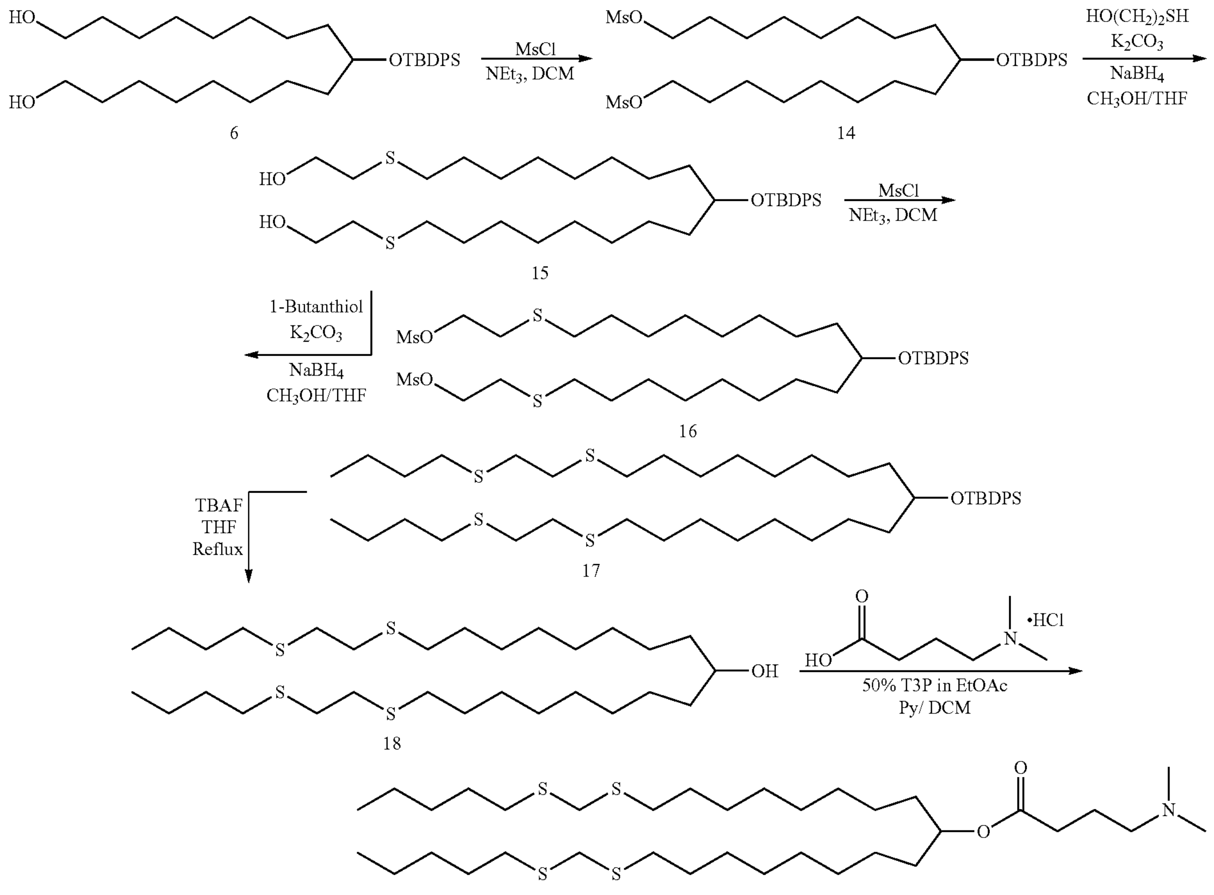

6, 14, 15, 16, 17, 18, 19

9-((tert-butyldiphenylsilyl)oxy)heptadecane-1,17-diyl dimethanesulfonate (14)

A solution of methanesulfonyl chloride (0.48 g, 4.2 mmol) in anhydrous dichloromethane (1 mL) was added dropwise to a cold (0° C.), stirred solution of 6 (1.05 g, 2.0 mmol) in dichloromethane (3 mL), under argon. Upon completion of the addition, the reaction mixture was allowed to warm to ambient temperature and stirred overnight, then it was diluted with dichloromethane (10 mL), sequentially washed with saturated aqueous sodium bicarbonate solution (3×5 mL), saturated aqueous ammonium chloride solution (2×5 mL), water (3×5 mL), and saturated aqueous sodium chloride solution (2×5 mL). The organic phase was dried over anhydrous sodium sulfate, filtered, and concentrated under reduced pressure. The residue was purified by column chromatography on silica gel (230-400 mesh) by eluting with 40% ethyl acetate in hexane. This afforded 1.0 g of

2,2'-((9-((tert-butyldiphenylsilyl)oxy)heptadecane-1,17-diyl)bis(sulfanediyl))bis(ethan-1-ol) (15)

Mesylate 14 (0.68 g, 1.0 mmol) was added to a solution of 2-mercaptoethanol (0.47 g, 6.0 mmol), sodium borohydride (0.076 g, 2.0 mmol) and $K_2CO_3$ (0.97 g, 7.0 mmol) in anhydrous 60% MeOH/THF (3 mL), and the resulting mixture was stirred at room temperature for 14 h. The solvent was removed under reduced pressure and the residue was dissolved in ethyl acetate (5 mL) and sequentially washed with saturated aqueous ammonium chloride solution (2×5 mL), saturated aqueous sodium bicarbonate solution (2×5 mL), water (2×5 mL), and saturated aqueous sodium chloride solution (2×5 mL). The organic phase was dried over anhydrous sodium sulfate, filtered through Celite®, and concentrated under reduced pressure. The residue was purified by column chromatography on silica gel (230-400 mesh) by eluting with 20-40% ethyl acetate in hexane. This afforded 0.45 g of product (70%) as a colorless oil. $^1$H NMR (300 MHz, $CDCl_3$): δ 7.68-7.65 (m, 4H), 7.43-7.32 (m, 6H), 3.74-3.69 (m, 5H), 2.73 (t, 4H, J=6.2 Hz), 2.50 (t, 4H, J=7.3 Hz), 2.17 (br, 2H), 1.61-1.51 (m, 4H), 1.40-1.33 (m, 8H), 1.27-1.14 (m, 16H), 1.04 (s, 9H) ppm. $^{13}C$ NMR (300 MHz, $CDCl_3$): δ 135.9, 134.8, 129.3, 127.3, 73.2, 60.1, 36.3, 35.3, 31.6, 29.7, 29.5, 29.4, 29.1, 28.8, 27.0, 24.8, 22.6, 19.4.

((9-((tert-butyldiphenylsilyl)oxy)heptadecane-1,17-diyl)bis(sulfanediyl))bis(ethane-2,1-diyl) dimethanesulfonate (16)

A solution of methanesulfonyl chloride (0.17 g, 1.47 mmol) in anhydrous dichloromethane (1 mL) was added dropwise to a cold (0° C.) solution of 15 (0.45 g, 0.70 mmol) and triethylamine (0.17 g, 1.68 mmol) in 2 mL of anhydrous dichloromethane, under argon. Upon completion of the addition, the reaction mixture was allowed to warm to ambient temperature and stirred overnight. The reaction mixture was diluted with dichloromethane (5 mL) and sequentially washed with saturated aqueous sodium bicarbonate solution (3×5 mL), saturated aqueous ammonium chloride solution (2×5 mL), water (3×5 mL), and saturated aqueous sodium chloride solution (3×5 mL). The organic phase was dried over anhydrous sodium sulfate, filtered through Celite®, and concentrated under reduced pressure to afford 0.5 g of product as a pale yellow oil, which was used in the next step without purification.

5-(8-((2-(butylthio)ethyl)thio)octyl)-2,2-dimethyl-3,3-diphenyl-4-oxa-14,17-dithia-3-silahenicosane (17)

Mesylate 16 (0.50 g, 0.62 mmol) was added to a solution of 1-butanethiol (0.34 g, 3.72 mmol), sodium borohydride (0.047 g, 1.24 mmol) and $K_2CO_3$ (0.60 g, 4.34 mmol) in anhydrous 60% MeOH/THF (2 mL), and the resulting mixture was stirred at room temperature for 14 h. The solvent was removed under reduced pressure and the residue was dissolved in ethyl acetate (5 mL) and sequentially washed with saturated aqueous sodium bicarbonate solution (3×5 mL), water (3×5 mL), and saturated aqueous sodium chloride solution (2×5 mL). The organic phase was dried over anhydrous sodium sulfate, filtered through Celite®, and concentrated under reduced pressure. The residue was purified by column chromatography on silica gel (230-400 mesh) by eluting with 0-5% ethyl acetate in hexane. This afforded 0.29 g of product 17 (60%) as a pale yellow oil. $^{1}H$ NMR (300 MHz, $CDCl_3$): δ 7.68-7.65 (m, 4H), 7.43-7.32 (m, 6H), 3.69 (quin, 1H, J=6.0 Hz), 2.71 (s, 8H), 2.52 (t, 8H, J=7.2 Hz), 1.61-1.51 (m, 8H), 1.40-1.32 (m, 12H), 1.27-1.13 (m, 16H), 1.04 (s, 9H), 0.92 (t, 6H, J=7.2 Hz) ppm. $^{13}C$ NMR (300 MHz, $CDCl_3$): δ 135.9, 134.8, 129.3, 127.3, 73.2, 36.3, 32.2, 32.1, 31.9, 31.8, 29.7, 29.6, 29.4, 29.1, 28.8, 27.1, 24.8, 22.0, 19.4, 13.7.

5,8,26,29-tetrathiatritriacontan-17-ol (18)

A mixture of TBDPS ether 17 (0.29 g, 0.37 mmol) and TBAF (1.0 M in THF, 3.7 mL, 3.7 mmol) was refluxed for 12 h. The solvent was removed under reduced pressure and the residue was dissolved in diethyl ether (5 mL), sequentially washed with saturated aqueous sodium bicarbonate solution (2×5 mL), water (2×5 mL), and saturated aqueous sodium chloride solution (2×5 mL). The organic phase was dried over anhydrous sodium sulfate, filtered through Celite®, and concentrated under reduced pressure. The residue was purified by column chromatography on silica gel (230-400 mesh) by eluting with 10% ethyl acetate in hexane. This afforded 0.16 g of product (80%) as white solid. $^{1}H$ NMR (300 MHz, $CDCl_3$): δ 3.57 (br, 1H), 2.71 (s, 8H), 2.52 (t, 8H, J=7.2 Hz), 1.61-1.51 (m, 9H), 1.40-1.13 (m, 28H), 0.92 (t, 6H, J=7.2 Hz) ppm. $^{13}C$ NMR (300 MHz, $CDCl_3$): δ 72.0, 37.5, 32.2, 32.19, 31.9, 31.8, 29.7, 29.6, 29.5, 29.2, 28.8, 21.9, 13.7.

5,8,26,29-tetrathiatritriacontan-17-yl 4-(dimethylamino)butanoate (19)

Propylphosphonic anhydride (T3P, 50% w/w in EtOAc, 0.37 g, 0.58 mmol) was added to a solution of alcohol 18 (0.16 g, 0.29 mmol), pyridine (0.046 g, 0.58 mmol), and the hydrochloride salt of dimethylaminobutyric acid (0.073 g, 0.44 mmol) 1 mL of anhydrous dichloromethane. The mixture was stirred at room temperature overnight, whereupon TLC analysis showed complete disappearance of the starting material. The solvent was removed under reduced pressure and the residue was dissolved in ethyl acetate (5 mL) and sequentially washed with saturated aqueous ammonium chloride solution (2×5 mL), water (2×5 mL), and saturated aqueous sodium chloride solution (2×5 mL). The organic phase was dried over anhydrous sodium sulfate, filtered through Celite®, and concentrated under reduced pressure. The crude product was purified by Flash column chromatography on silica gel (230-400 mesh) by eluting with 5-15% ethyl acetate in 0.5% $NEt_3$ in hexane to afford 0.14 g of product (70%) as a pale yellow oil. $^{1}H$ NMR (300 MHz, $CDCl_3$): δ 4.86 (quin, 1H, J=6.0 Hz), 2.71 (s, 8H), 2.54 (t, 8H, J=7.2 Hz), 2.25-2.34 (m, 4H), 2.21 (s, 6H), 1.83-1.73 (m, 2H), 1.64-1.26 (m, 36H), 0.91 (t, 6H, J=7.2 Hz) ppm. $^{13}C$ NMR (300 MHz, $CDCl_3$): δ 173.4, 74.2, 58.9, 45.4, 34.1, 32.5, 32.2, 32.1, 31.9, 31.8, 29.7, 29.5, 29.4, 29.2, 28.8, 25.3, 23.1, 21.9, 13.7.

Example 3: Synthesis of Cationic Ionizable Lipid 4,8,26,30-tetrathiatritriacontan-17-yl 4-(dimethylamino)butanoate (24)

The synthesis of the cationic ionizable lipid 4,8,26,30-tetrathiatritriacontan-17-yl 4-(dimethylamino)butanoate (24) is show in the Scheme below, followed by a description of the synthesis of each intermediate thereof.

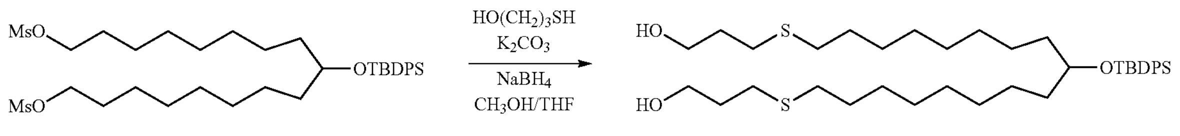

14 20

-continued

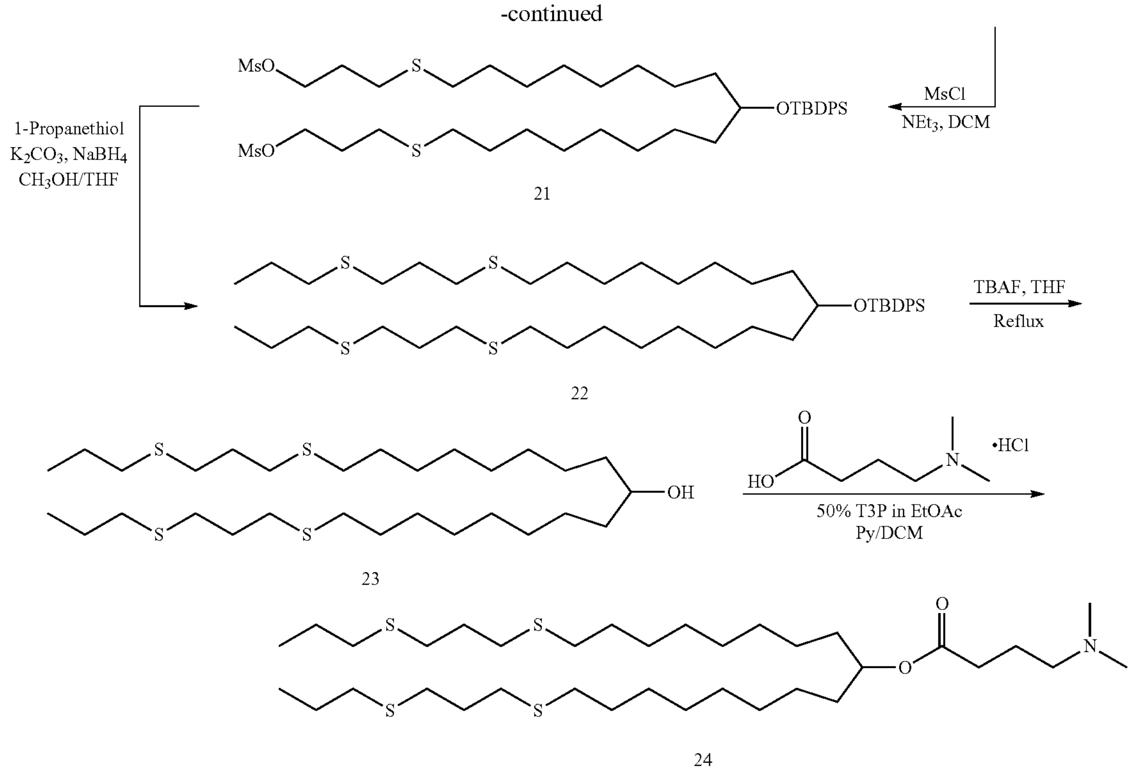

3,3'-((9-((tert-butyldiphenylsilyl)oxy)heptadecane-1,17-diyl)bis(sulfanediyl))bis(propan-1-ol) (20)

Mesylate 14 (0.68 g, 1.0 mmol) was added to a solution of 3-mercapto-1-propanol (0.55 g, 6.0 mmol), sodium borohydride (0.076 g, 2.0 mmol) and $K_2CO_3$ (0.97 g, 7.0 mmol) in anhydrous 60% MeOH/THF (3 mL), under argon. The mixture was stirred at room temperature for 14 h. The solvent was removed under reduced pressure and the residue was dissolved in ethyl acetate (5 mL) and sequentially washed with saturated aqueous ammonium chloride solution (2×5 mL), saturated aqueous sodium bicarbonate solution (2×5 mL), water (2×5 mL), and saturated aqueous sodium chloride solution (2×5 mL). The organic phase was dried over anhydrous sodium sulfate, filtered through Celite®, and concentrated under reduced pressure. The residue was purified by column chromatography on silica gel (230-400 mesh) by eluting with 20-40% ethyl acetate in hexane. This afforded 0.51 g of product (75%) as a colorless oil. $^1$H NMR (300 MHz, $CDCl_3$): δ 7.68-7.65 (m, 4H), 7.43-7.32 (m, 6H), 3.77-3.69 (m, 5H), 2.63 (t, 4H, J=6.9 Hz), 2.51 (t, 4H, J=7.5 Hz), 1.89-1.83 (m, 6H), 1.61-1.51 (m, 4H), 1.40-1.33 (m, 8H), 1.27-1.14 (m, 16H), 1.04 (s, 9H) ppm. $^{13}$C NMR (300 MHz, $CDCl_3$): δ 135.9, 134.8, 129.3, 127.3, 73.2, 62.0, 36.3, 32.1, 31.9, 29.6, 29.4, 29.1, 28.9, 27.1, 24.8, 19.4.

((9-((tert-butyldiphenylsilyl)oxy)heptadecane-1,17-diyl)bis(sulfanediyl))bis(propane-3,1-diyl) dimethanesulfonate (21)

A solution of methanesulfonyl chloride (0.18 g, 1.60 mmol) in anhydrous dichloromethane (1 mL) was added dropwise to a cold (0° C.), stirred solution of 20 (0.51 g, 0.76 mmol) and triethylamine (0.18 g, 1.82 mmol) in 2 mL of anhydrous dichloromethane. Upon completion of the addition, the reaction mixture was allowed to warm to ambient temperature and stirred overnight. The reaction mixture was diluted with dichloromethane (5 mL), sequentially washed with saturated aqueous sodium bicarbonate solution (3×5 mL), saturated aqueous ammonium chloride solution (2×5 mL), water (3×5 mL), and saturated aqueous sodium chloride solution (3×5 mL). The organic phase was dried over anhydrous sodium sulfate, filtered through Celite®, and concentrated under reduced pressure to afford 0.6 g of mesylate 21 as pale yellow oil, which was used in the next step without further purification.

2,2-dimethyl-3,3-diphenyl-5-(8-((3-(propylthio)propyl)thio)octyl)-4-oxa-14,18-dithia-3-silahenicosane (22)

Mesylate 21 (0.60 g, ca. 0.72 mmol) was added to a solution of 1-propanethiol (0.33 g, 4.32 mmol), sodium borohydride (0.054 g, 1.44 mmol) and $K_2CO_3$ (0.70 g, 5.04 mmol) in anhydrous 60% MeOH/THF (2 mL), and the resulting mixture was stirred at room temperature for 14 h. The solvent was removed under reduced pressure and the residue was dissolved in ethyl acetate (5 mL) and sequentially washed with saturated aqueous sodium bicarbonate solution (3×5 mL), water (3×5 mL), and saturated aqueous sodium chloride solution (2×5 mL). The organic phase was dried over anhydrous sodium sulfate, filtered through Celite®, and concentrated under reduced pressure. The residue was purified by column chromatography on silica gel (230-400 mesh) by eluting with 0-5% ethyl acetate in hexane. This afforded 0.34 g of product 22 (60%) as a pale yellow oil. $^1$H NMR (300 MHz, $CDCl_3$): δ 7.68-7.65 (m, 4H), 7.43-7.32 (m, 6H), 3.68 (quin, 1H, J=6.3 Hz), 2.61 (t, 8H, J=7.2 Hz), 2.49 (t, 8H, J=7.2 Hz), 1.90-1.80 (m, 4H), 1.62-1.53 (m, 8H), 1.40-1.32 (m, 8H), 1.27-1.13 (m, 16H), 1.04 (s, 9H), 0.98 (t, 6H, J=7.5 Hz) ppm. $^{13}C$ NMR (300 MHz, $CDCl_3$): δ 135.9, 134.8, 129.3, 127.3, 73.2, 36.3, 34.2, 32.2, 31.0, 30.9, 29.7, 29.6, 29.5, 29.4, 29.2, 28.9, 27.0, 24.8, 22.9, 19.4, 13.5.

4,8,26,30-tetrathiatritriacontan-17-ol (23)

A solution of 22 (0.34 g, 0.43 mmol) and TBAF (1.0 M in THF, 4.3 mL, 4.3 mmol) was refluxed for 12 h. The solvent was removed under reduced pressure and the residue was dissolved in diethyl ether (5 mL) and sequentially washed with saturated aqueous sodium bicarbonate solution (2×5 mL), water (2×5 mL), and saturated aqueous sodium chloride solution (2×5 mL). The organic phase was dried over anhydrous sodium sulfate, filtered through Celite®, and concentrated under reduced pressure. The residue was purified by column chromatography on silica gel (230-400 mesh) by eluting with 15% ethyl acetate in hexane. This afforded 0.21 g of product (85%) as white solid. $^1H$ NMR (300 MHz, $CDCl_3$): δ 3.57 (br, 1H), 2.60 (t, 8H, J=7.2 Hz), 2.49 (t, 8H, J=7.0 Hz), 1.90-1.80 (m, 4H), 1.67-1.52 (m, 9H), 1.42-1.29 (m, 24H), 0.98 (t, 6H, J=7.2 Hz) ppm. $^{13}C$ NMR (300 MHz, $CDCl_3$): δ 71.9, 37.5, 34.2, 32.1, 31.0, 30.9, 29.6, 29.5, 29.4, 29.2, 28.9, 25.6, 22.9, 13.5.

over anhydrous sodium sulfate, filtered through Celite®, and concentrated under reduced pressure. The crude product was purified by Flash column chromatography on silica gel (230-400 mesh) by eluting with 5-15% ethyl acetate in 0.5% $NEt_3$ in hexane to afford 0.18 g of product (70%) as a pale yellow oil. $^1H$ NMR (300 MHz, $CDCl_3$): δ 4.85 (quin, 1H, J=6.3 Hz), 2.59 (t, 8H, J=7.5 Hz), 2.48 (t, 8H, J=7.5 Hz), 2.24-2.33 (m, 4H), 2.20 (s, 6H), 1.89-1.75 (m, 6H), 1.63-1.48 (m, 12H), 1.34-1.25 (m, 20H), 0.97 (t, 6H, J=7.5 Hz) ppm. $^{13}C$ NMR (300 MHz, $CDCl_3$): δ 173.4, 74.2, 58.9, 45.4, 34.2, 34.1, 32.4, 32.1, 31.0, 30.9, 29.6, 29.43, 29.4, 29.39, 29.1, 28.9, 25.3, 23.1, 22.9, 13.5.

Example 4: Synthesis of Cationic Ionizable Lipid 3-((6,8,26,28-tetrathiatritriacontan-17-yl)thio)-N,N-dimethylpropan-1-amine (28)

The synthesis of the cationic ionizable lipid 3-((6,8,26,28-tetrathiatritriacontan-17-yl)thio)-N,N-dimethylpropan-1-amine (28) is show in the Scheme below, followed by a description of the synthesis of each intermediate thereof.

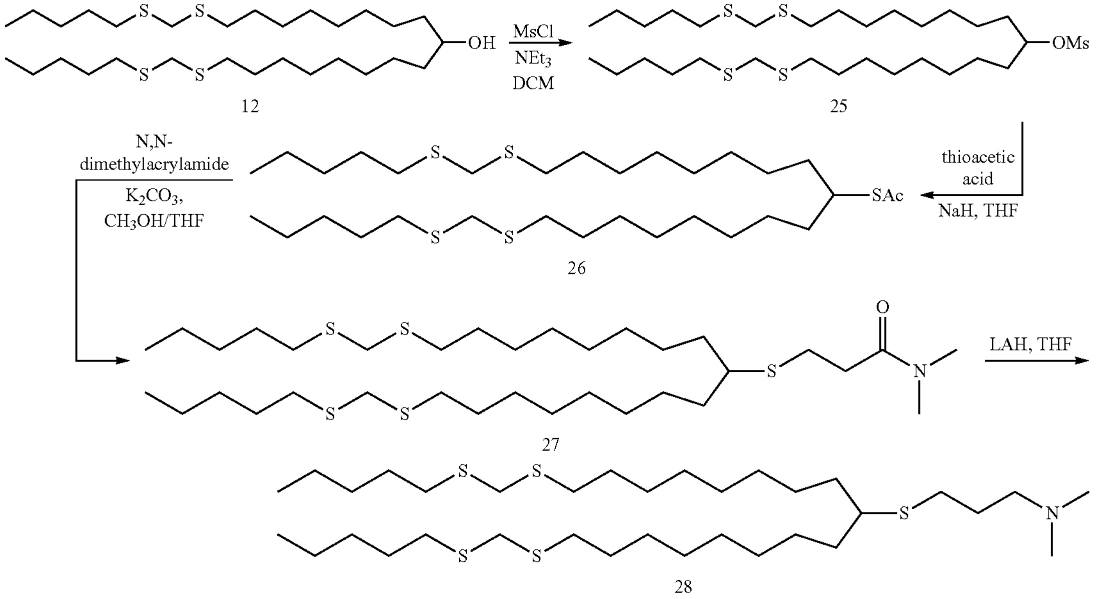

4,8,26,30-tetrathiatritriacontan-17-yl 4-(dimethylamino)butanoate (24)

Propylphosphonic anhydride (T3P, 50% w/w in EtOAc, 0.48 g, 0.76 mmol) was added to a solution of alcohol 23 (0.21 g, 0.38 mmol) and pyridine (0.060 g, 0.76 mmol) in 1 mL of anhydrous dichloromethane. The mixture was stirred at room temperature overnight, whereupon TLC analysis showed complete disappearance of the starting material. The solvent was removed under reduced pressure and the residue was dissolved in ethyl acetate (5 mL) and was sequentially washed with saturated aqueous ammonium chloride solution (2×5 mL), water (2×5 mL), and saturated aqueous sodium chloride solution (2×5 mL). The organic phase was dried 6,8,26,28-tetrathiatritriacontan-17-yl methanesulfonate (25)

A solution of methanesulfonyl chloride (0.15 g, 1.3 mmol) in anhydrous dichloromethane (1 mL) was added dropwise to a cold (0° C.), stirred solution of 12 (0.55 g, 1.0 mmol) and triethylamine (0.15 g, 1.5 mmol) in 4 mL of anhydrous dichloromethane, under argon. Upon completion of the addition, the reaction mixture was allowed to warm to ambient temperature and stirred overnight. The reaction mixture was diluted with dichloromethane (10 mL) and sequentially washed with saturated aqueous sodium bicarbonate solution (2×5 mL), water (2×5 mL), and saturated aqueous sodium chloride solution (2×5 mL). The organic phase was dried over anhydrous sodium sulfate, filtered, and concentrated under reduced pressure. The residue was purified by column chromatography on silica gel (230-400 mesh) by eluting with 20% ethyl acetate in hexane. This afforded 0.43 g of product (70%) as colorless oil. $^1H$ NMR (300 MHz, $CDCl_3$): δ 4.69 (quin, 1H, J=6.0 Hz), 3.65 (s, 4H), 2.99 (s, 3H), 2.61 (t, 8H, J=7.5 Hz), 1.68-1.56 (m, 12H), 1.36-1.29 (m, 28H), 0.89 (t, 6H) ppm. $^{13}C$ NMR (300 MHz, $CDCl_3$): δ 84.2, 39.1, 38.8, 35.4, 34.4, 31.0, 30.8, 29.31, 29.1, 29.0, 28.8, 28.7, 24.9, 22.3, 14.0.

S-(6,8,26,28-tetrathiatritriacontan-17-yl) ethanethioate (26)

Sodium hydride (57% dispersion oil, 0.23 g, 5.44 mmol) in a 10 mL round bottom flask sealed under argon was washed with pentane three times, then it was suspended in dry THF (1 mL). The suspension was cooled to 0° C. (ice bath) and a solution of thioacetic acid (0.42 g, 5.44 mmol) in THF (0.5 mL) was added dropwise via syringe (CAUTION: vigorous $H_2$ evolution). The resulting mixture was stirred at room temperature for 30 minutes, then a solution of 25 (0.43 g, 0.68 mmol) in 0.5 mL of dry THF was added dropwise and the mixture was stirred overnight. The solvent was removed under reduced pressure and deionized water $H_2O$ (5 mL) was carefully added (CAUTION: vigorous reaction, evolution of $H_2$). The mixture was extracted with diethyl ether (3×5 mL) and the combined extracts were sequentially washed with $H_2O$ (5 mL) and saturated aqueous sodium chloride solution (2×5 mL). The organic phase was dried over anhydrous sodium sulfate, filtered through Celite®, and concentrated under reduced pressure to afford 0.42 g of product 26 as yellowish oil, which was used in the next step without purification.

3-((6,8,26,28-tetrathiatritriacontan-17-yl)thio)-N,N-dimethylpropanamide (27)

A mixture of compound 26 and $K_2CO_3$ (0.38 g, 2.72 mmol) in anhydrous 60% MeOH/THF (2 mL) was stirred at ambient temperature for 4 h, then N,N-dimethylacrylamide (0.13 g, 1.36 mmol) was added slowly and the reaction mixture was stirred overnight. The solvent was removed under reduced pressure and the residue was dissolved in diethyl ether (5 mL) and sequentially washed with aqueous HCl (1M, 2×5 mL), saturated aqueous sodium bicarbonate solution (2×5 mL), water (2×5 mL), and saturated aqueous sodium chloride solution (2×5 mL). The organic phase were dried over anhydrous sodium sulfate, filtered through Celite®, and concentrated under reduced pressure. The residue was purified by column chromatography on silica gel (230-400 mesh) by eluting with 30% ethyl acetate in hexane. This afforded 0.12 g, 27% of product as a pale yellow oil. $^1H$ NMR (300 MHz, $CDCl_3$): δ 3.63 (s, 4H), 3.01 (s, 6H), 2.99-2.94 (m, 4H), 2.62-2.58 (m, 9H), 1.64-1.48 (m, 12H), 1.41-1.27 (m, 28H), 0.89 (t, 6H, J=6.6 Hz) ppm.

3-((6,8,26,28-tetrathiatritriacontan-17-yl)thio)-N,N-dimethylpropan-1-amine (28)

A solution of 27 (0.12 g, 0. 0.18 mmol) in 0.1 mL of dry THF was added dropwise to a cold (0° C.), stirred suspension of $LiAlH_4$ (0.008 g, 0.22 mmol) in 0.2 mL of dry THF, under argon. Upon completion of the addition, the mixture was allowed to warm up to room temperature and stirred at room temperature for 4 hours. The mixture was cooled back to 0° C., diluted with diethyl ether, and sequentially treated with water (10 μL), 15% aqueous NaOH solution (10 μL), and more water (30 μL). The resulting suspension was allowed to warm up to room temperature and stirred for 15 minutes, then it was filtered through Celite® and the solids were was washed with ether (3×3 mL). The combine filtrates were dried over sodium sulfate and concentrated under vacuum. The crude product was purified by column chromatography on silica gel (230-400 mesh) by eluting with 0-5% methanol in dichloromethane to afford lipid 28 (0.09 g, 80%) as a colorless oil. $^1H$ NMR (300 MHz, $CDCl_3$): δ 3.63 (s, 4H), 2.71 (t, 2H, J=7.2 Hz), 2.61 (t, 8H, J=7.2 Hz), 2.52-2.47 (m, 1H), 2.39 (t, 2H, J=7.5 Hz), 2.24 (s, 6H), 1.94-1.84 (m, 2H), 1.66-1.55 (m, 16H), 1.40-1.24 (m, 24H), 0.89 (t, 6H, J=6.6 Hz) ppm.

Example 5: Synthesis of Cationic Ionizable Lipid 3-((6Z,9Z,28Z,31Z)-heptatriaconta-6,9,28,31-tetraen-19-ylthio)-N,N-dimethylpropan-1-amine (33)

The synthesis of the cationic ionizable lipid 3-((6Z,9Z,28Z,31Z)-heptatriaconta-6,9,28,31-tetraen-19-ylthio)-N,N-dimethylpropan-1-amine (33) is show in the Scheme below, followed by a description of the synthesis of each intermediate thereof.

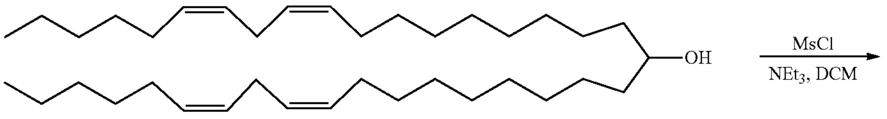

29

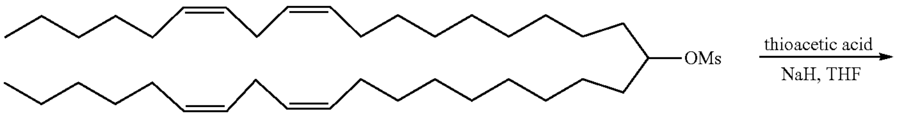

30

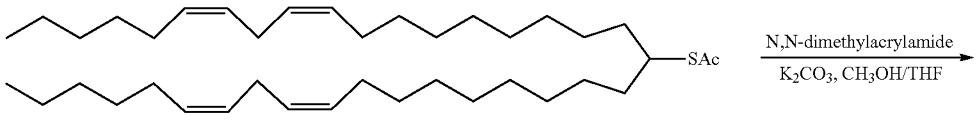

31

-continued

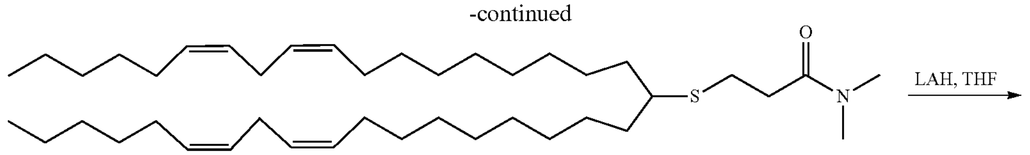

32

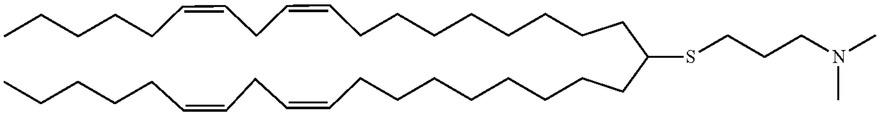

33

The synthesis of each intermediate in the above scheme is set forth below.

Synthesis of (6Z,9Z,28Z,31Z)-heptatriaconta-6,9,28,31-tetraen-19-yl methanesulfonate (30)

(6Z,9Z,28Z,31Z)-Heptatriaconta-6,9,28,31-tetraen-19-ol, 29, was synthesized as reported earlier[4] and its spectral data matched with the reported values. A solution of methanesulfonyl chloride (0.14 g, 1.2 mmol) in anhydrous dichloromethane (1 mL) was added dropwise to a cold (0° C.) solution of alcohol 29 and triethylamine (0.13 g, 1.3 mmol) in 2 mL of anhydrous dichloromethane. Upon completion of the addition, the reaction mixture was allowed to warm to ambient temperature and stirred overnight. The reaction mixture was diluted with dichloromethane (10 mL), sequentially washed with saturated aqueous sodium bicarbonate solution (2×5 mL), water (2×5 mL) and saturated aqueous sodium chloride solution (2×5 mL). The organic phase was dried over anhydrous sodium sulfate, filtered, and concentrated under reduced pressure. The residue was purified by column chromatography on silica gel (230-400 mesh) by eluting with 0-10% ethyl acetate in hexane. This afforded 0.57 g of product (93%) as a colorless oil. $^{1}$H NMR (300 MHz, $CDCl_3$): δ 5.42-5.28 (m, 8H), 4.69 (quin, 1H, J=6.0 Hz), 2.98 (s, 3H), 2.77 (t, 4H, J=6.0 Hz), 2.04 (q, 8H, J1=6.6, J2=13.5 Hz), 1.68-1.64 (m, 4H), 1.37-1.29 (m, 36H), 0.90 (t, 6H, J=6.9 Hz) ppm. $^{13}$C NMR (300 MHz, $CDCl_3$): δ 130.1, 130.0, 127.9, 127.8, 84.3, 38.6, 31.5, 29.6, 29.41, 29.4, 29.36, 29.3, 29.2, 27.2, 25.6, 24.9, 22.5, 14.0.

Synthesis of S-((6Z,9Z,28Z,31Z)-heptatriaconta-6,9,28,31-tetraen-19-yl) ethanethioate (31)

Sodium hydride (57% dispersion oil, 0.16 g, 3.76 mmol) in a 10 mL round bottom flask sealed under argon was washed with pentane three times, then it was suspended in dry THF (1 mL) and the suspension was cooled in an ice bath. A solution of thioacetic acid (0.29 g, 3.76 mmol) in THF (0.5 mL) was added dropwise to the cold, stirred suspension (CAUTION: vigorous evolution of $H_2$). The resulting mixture was allowed to warm to room temperature and stirred for 30 minutes, then a solution of 30 (0.57 g, 0.94 mmol) in 0.5 mL of dry THF was added dropwise and the mixture was stirred overnight. The solvent was removed under reduced pressure and deionized water $H_2O$ (5 mL) was added. The mixture was extracted with diethyl ether (3×5 mL) and the combined extracts were sequentially washed with $H_2O$ (5 ml) and saturated aqueous sodium chloride solution (2×5 mL). The organic phase was dried over anhydrous sodium sulfate, filtered through Celite®, and concentrated under reduced pressure. Purification of the crude product by column chromatography on silica gel (230-400 mesh) by eluting with 0-3% hexane/diethyl ether provided 31 (0.30 g, 55%) as a pale yellow oil. $^{1}$H NMR (300 MHz, $CDCl_3$): δ 5.36-5.28 (m, 8H), 3.50 (quin, 1H, J=6.0 Hz), 2.77 (t, 4H, J=6.0 Hz), 2.31 (s, 3H), 2.05 (q, 8H, J1=6.1, J2=12.8 Hz), 1.58-1.53 (m, 4H), 1.30-1.27 (m, 36H), 0.89 (t, 6H, J=6.7 Hz) ppm. $^{13}$C NMR (300 MHz, $CDCl_3$): δ 193.9, 130.1, 130.0, 127.9, 127.8, 60.3, 41.2, 38.6, 31.5, 29.6, 29.44, 29.4, 29.36, 29.3, 29.2, 27.2, 25.6, 22.5, 14.0.

3-(((6Z,9Z,28Z,31Z)-heptatriaconta-6,9,28,31-tetraen-19-yl)thio)-N,N-dimethylpropanamide (32)

A mixture of compound 31 (0.30 g, 0.51 mmol) and $K_2CO_3$ (0.21 g, 1.5 mmol) in anhydrous 60% MeOH/THF (2 mL) was stirred at ambient temperature for 4 h, then N,N-dimethylacrylamide (0.10 g, 1.0 mmol) was added slowly and the reaction mixture was stirred overnight. The solvent was removed under reduced pressure and the residue was dissolved in diethyl ether (5 mL) and sequentially washed with aqueous HCl (1M, 2×5 mL), saturated aqueous sodium bicarbonate solution (2×5 mL), water (2×5 mL), and saturated aqueous sodium chloride solution (2×5 mL). The organic phase was dried over anhydrous sodium sulfate, filtered through Celite®, and concentrated under reduced pressure. The residue was purified by column chromatography on silica gel (230-400 mesh) by eluting with 30% ethyl acetate in hexane. This afforded 0.18 g of product (55%) as a colorless oil. $^{1}$H NMR (300 MHz, $CDCl_3$): δ 5.36-5.28 (m, 8H), 2.97 (s, 6H), 2.79-2.75 (m, 6H), 2.59-2.57 (m, 3H), 2.04 (q, 8H, J1=6.3, J2=12.9 Hz), 1.54-1.50 (m, 4H), 1.40-1.28 (m, 36H), 0.89 (t, 6H, J=6.9 Hz) ppm. $^{13}$C NMR (300 MHz, $CDCl_3$): δ 171.3, 130.19, 130.16, 127.9, 46.6, 34.8, 33.9, 31.5, 29.7, 29.6, 29.5, 29.34, 29.3, 27.2, 26.9, 25.6, 22.6, 14.0.

3-((6Z,9Z,28Z,31Z)-heptatriaconta-6,9,28,31-tetraen-19-ylthio)-N,N-dimethylpropan-1-amine (33)

A solution of 32 (0.18 g, 0.28 mmol) in 0.1 mL of dry THF was added dropwise to a cold (0° C.) suspension of $LiAlH_4$ (0.012 g, 0.34 mmol) in 0.3 mL of dry THF, under argon. Upon completion of the addition, the suspension was allowed to warm up to room temperature and stirred at room temperature for 4 hours. The mixture was chilled in an ice bath, diluted with diethyl ether, and sequentially treated with $H_2O$ (0.012 mL), 15% aqueous sodium hydroxide (0.012 mL) and $H_2O$ (0.036 mL). The resulting suspension was allowed to warm to room temperature and stirred for 15 minutes, then it was filtered through Celite® and the solids were washed with ether (4×5 mL). The combined filtrates were dried over sodium sulfate and concentrated under vacuum. The residue was purified by column chromatography on silica gel (230-400 mesh) by eluting with 0-5% methanol in dichloromethane to afford lipid 33 (0.16 g, 92%) as a colorless oil. $^1$H NMR (300 MHz, $CDCl_3$): δ 5.36-5.28 (m, 8H), 2.79-2.75 (m, 4H), 2.58-2.48 (m, 3H), 2.37 (t, 2H, J=7.5 Hz), 2.24 (s, 6H), 2.04 (q, 8H, J1=6.3, J2=12.9 Hz), 1.74 (quin, 2H, J=7.5 Hz), 1.54-1.50 (m, 4H), 1.40-1.28 (m, 36H), 0.89 (t, 6H, J=6.9 Hz) ppm. $^{13}$C NMR (300 MHz, $CDCl_3$): δ 130.18, 130.15, 127.95, 127.93, 58.9, 46.0, 45.4, 34.8, 31.5, 29.7, 29.6, 29.5, 29.34, 29.3, 27.2, 26.8, 25.6, 22.6, 14.0.

Example 6: Lipid Nanoparticles Containing Sulfur-Containing Lipid and mRNA

LNPs were prepared comprising ionizable cationic sulfur-containing lipid/DSPC/cholesterol/PEG-lipid at molar ratios of 50/10/38.5/1.5 and mRNA (at N/P ratio of 6) as described in the Materials and Methods. The size, PDI and entrapment percentage were determined as set out in the Materials and Methods and the results are shown in Table 2 below. The data are based on n≥3 experiments and values reported are means±SD. Advantageously, the polydispersity index (PDI) of the resulting nanoparticles was <0.1, with an average LNP size ~80 nm.

TABLE 2

Physicochemical characteristics of LNPs comprising mRNA and sulfur lipid

| Sulfur Lipid | Size (nm) | PDI (nm) | Entrapment (%) |
|---|---|---|---|
| compound 13 | 79 | 0.054 | >93% |

Cryogenic transmission electron microscopy (cryo-TEM) images of the above LNPs entrapping mRNA are shown in FIG. 1.

Figure 2:
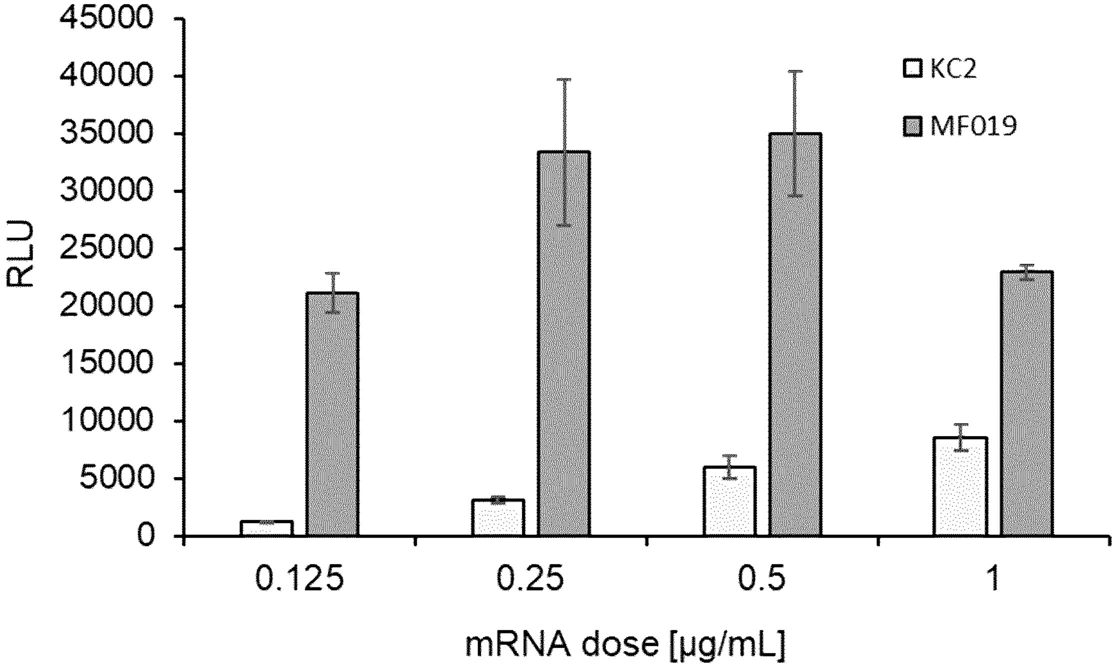
FIG. 2 shows in vitro gene expression efficacy of LNP systems entrapping mRNA encoding for firefly luciferase. HepG2 cells were treated different doses of LNP-mRNA systems composed of ionizable cationic lipid/DSPC/cholesterol/PEG-lipid (50/10/38.5/1.5). Luciferase expression was analyzed 24 hours post treatment. Ionizable cationic lipid used was either KC2 (DLin-KC2-DMA) or compound 13 (MF019).

The in vitro gene expression efficacy of LNP systems entrapping mRNA encoding for firefly luciferase was assessed. HepG2 cells were treated at different doses (0.125, 0.25, 0.5 and 1 μg/mL) using the above LNP-mRNA systems. Luciferase expression was analyzed 24 hours post treatment. Ionizable cationic lipid used was either KC2 (DLin-KC2-DMA) or compound 13 (MF019; see Example 1). The results represented as relative light unit (RLU) vs mRNA dose for KC2 and compound 13 (MF019) are shown in FIG. 2. In each case, the RLU was higher for compound 13 (MF019) than for KC2.

Figure 3:
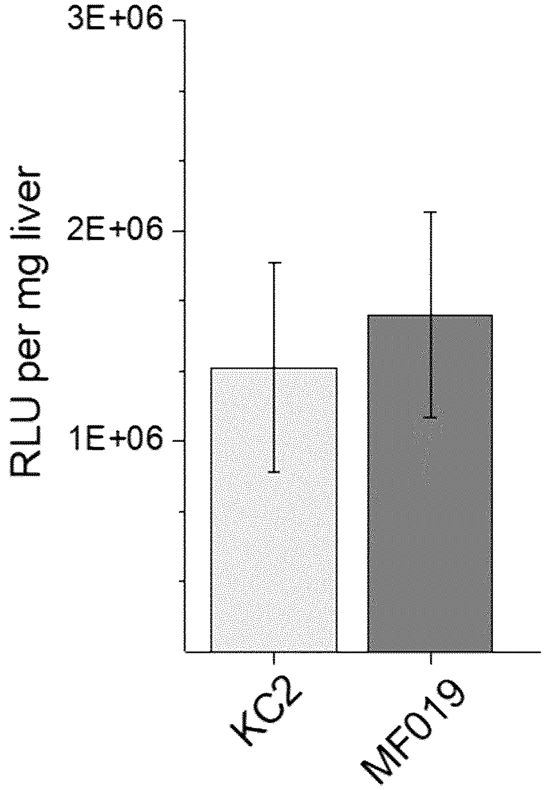
FIG. 3 shows in vivo gene expression efficacy of LNP systems entrapping mRNA encoding for firefly luciferase. Hepatic luciferase expression was analyzed 4 hours post intravenous administration of LNP-mRNA systems composed of ionizable cationic lipid/DSPC/cholesterol/PEG-lipid (50/10/38.5/1.5). Ionizable cationic lipid used was either KC2 or compound 13 (MF019).

FIG. 3 shows the in vivo gene expression efficacy of the LNP systems of this example entrapping mRNA encoding for firefly luciferase. Hepatic luciferase expression was analyzed 4 hours post intravenous administration of LNP-mRNA systems and the ionizable cationic lipid used was either KC2 (DLin-KC2-DMA) or compound 13 (MF019).

Example 7: Lipid Nanoparticles Containing Sulfur-Containing Lipid and mRNA

LNPs were prepared composed of ionizable cationic sulfur-containing lipid/DSPC/cholesterol/PEG-lipid at molar ratios of 50/10/38.5/1.5 and siRNA (at N/P ratio of 3) as described in the above Methods and Materials. The data are based on n≥3 experiments and values reported are means±SD.

Figure 4:
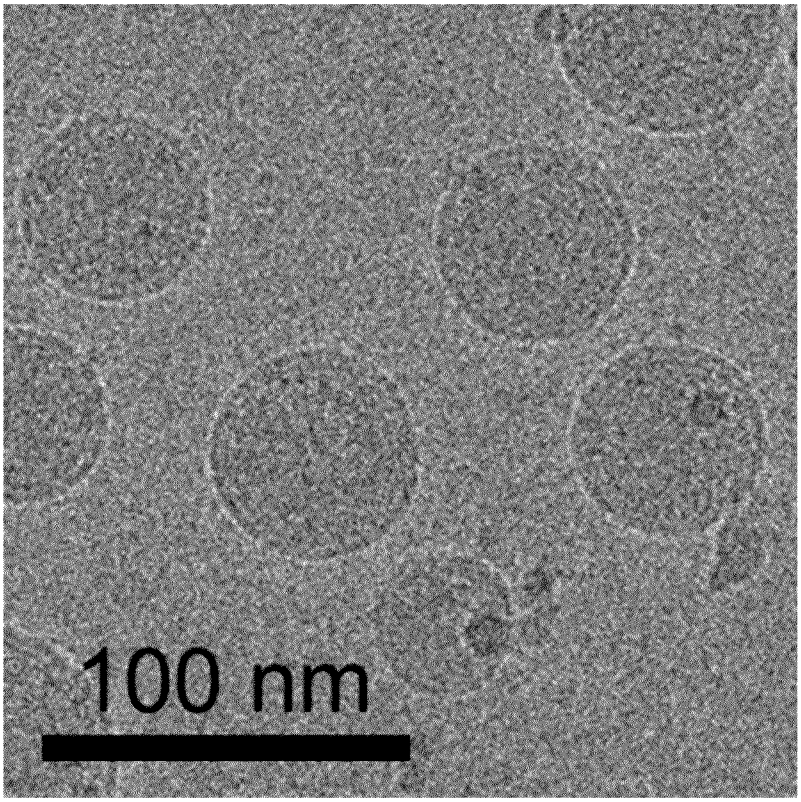
FIG. 4 shows cryo-TEM analysis of LNP entrapping siRNA. LNPs were composed of compound 13 (MF019)/DSPC/cholesterol/PEG-lipid at molar ratios of 50/10/38.5/1.5.

Compound 13 (MF019; see Example 1) produced siRNA formulations having desirable physicochemical characteristics as shown in Table 3 below. The polydispersity index (PDI) of the resulting nanoparticles was <0.1, with an average LNP size ~45 nm. The compound exhibited a pKa of 6.41 and, advantageously, the extent of siRNA entrapment of >93%. Cryo-TEM images of the siRNA formulations are shown in FIG. 4.

TABLE 3

Physicochemical characteristics of lipid nanoparticle (LNP) entrapping siRNA

| Sulfur Lipid | Size (nm) | PDI (nm) | Entrapment (%) | apparent pKa |
|---|---|---|---|---|
| compound 13 | 43 | 0.028 | >93% | 6.41 |

Figure 5A:
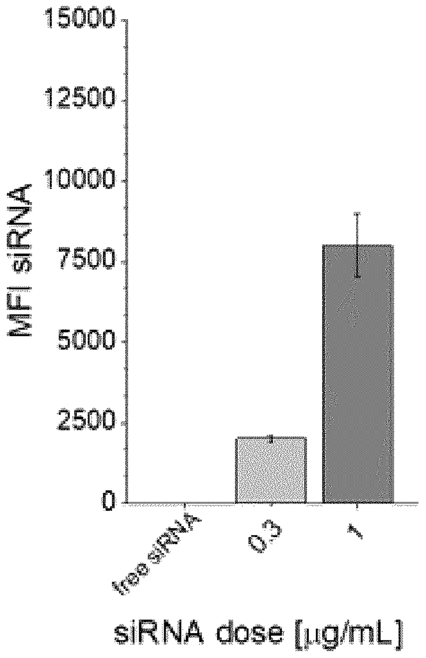
FIG. 5A-B shows in vitro gene silencing efficacy of LNP entrapping siRNA. H1299-dGFP cells were treated with free siRNA (1 μg/mL) or different doses of LNP-siRNA composed of compound 13/DSPC/cholesterol/PEG-lipid (50/10/38.5/1.5). (A) LNP-siRNA uptake was analyzed 24 hours post treatment using Alexa Fluor 647 modified siRNA. (B) Silencing of dGFP was analyzed 72 hours post treatment. Mean Fluorescence Intensity (MFI) values are given.
Figure 5B:
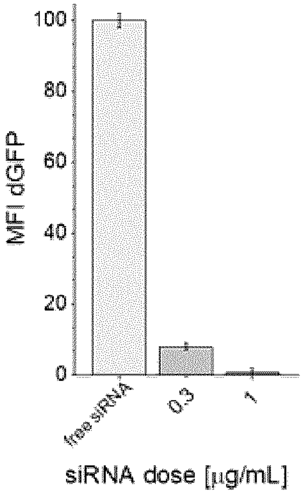

FIG. 5A-B shows in vitro gene silencing efficacy of the above LNPs entrapping siRNA. H1299-dGFP cells were treated with free siRNA (1 μg/mL) or different doses of LNP-siRNA and LNP-siRNA uptake was analyzed 24 hours post treatment using Alexa Fluor 647 modified siRNA (FIG. 5A). Silencing of dGFP was analyzed 72 hours post treatment (FIG. 5B). FIG. 5A and FIG. 5B respectively demonstrate effective siRNA uptake and gene silencing (showing Mean Fluorescence Intensity (MFI) values).

Figure 6:
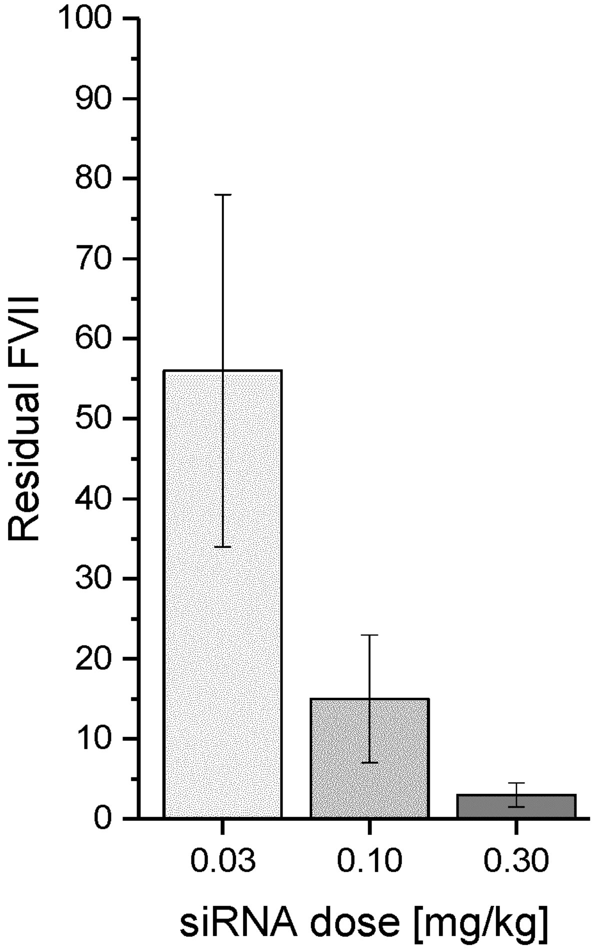
FIG. 6 shows in vivo gene silencing efficacy of LNP entrapping siRNA. The graph depicts residual Factor VII following intravenous administration of various doses LNP-siFVII composed of compound 13/DSPC/cholesterol/PEG-lipid (50/10/38.5/1.5).

In terms of efficacy in the standard Factor VII assay (see Materials and Methods), compound 13 has potent activity with almost complete knock down at 0.3 mg/kg. This is shown in FIG. 6, which shows in vivo gene silencing efficacy of LNP entrapping siRNA. The graph depicts residual Factor VII following intravenous administration of various doses of the LNP-siFVII (see Materials and Methods above).

Although the invention has been described and illustrated with reference to the foregoing detailed description and examples, it will be apparent that a variety of modifications and changes may be made without departing from the invention.

REFERENCES

1. Kulkarni, J. A. et al. On the Formation and Morphology of Lipid Nanoparticles Containing Ionizable Cationic Lipids and siRNA. *ACS Nano* 12, 4787-4795 (2018).
2. Kulkarni, J. A. et al. Fusion-dependent formation of lipid nanoparticles containing macromolecular payloads. *Nanoscale* 11, 9023-9031 (2019).
3. Chen, S. et al. Influence of particle size on the in vivo potency of lipid nanoparticle formulations of siRNA. *J Control Release J Control Release Soc* 235, 236-244 (2016).
4. Sean C., et al. Rational design of cationic lipids for siRNA delivery. *Nat. Biotechnol.* 28, 172-176 (2010).

The invention claimed is:

1. A compound having a structure of Formula I:

Formula I

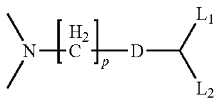

wherein:

D is S, O or an ester;

p is 1 to 6;

$L_1$ and/or $L_2$ are independently linear or branched $C_1$-$C_{30}$ alkyl, optionally having one or more C═C double bonds of E or Z geometry;

and wherein:

if D is S then $L_1$ and/or $L_2$ are unsubstituted or substituted with one or more S; and if D is O or the ester, then $L_1$ and/or $L_2$ are substituted with one more S.

2. The compound of claim 1, wherein D is O or

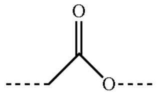

and the

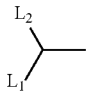

moiety of Formula I has the structure:

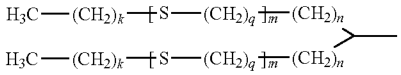

wherein n are independently 1 to 8;

m is one or more;

q are independently 1 to 8; and k is 1 to 8.

3. The compound of claim 2, wherein the m is; at least 2; 1 to 5; 2 or 3; or 2.

4. The compound of claim 1, wherein the k is 2 to 6.

5. The compound of claim 2, having the structure of Formula II:

Formula II

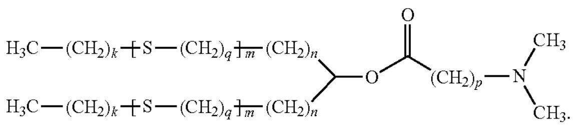

6. The compound of claim 5, wherein the m are each independently: 1 to 5; 2 or 3; or 2.

7. The compound of claim 5, wherein the k are each independently 2 to 6.

8. The compound of claim 1 having the structure of Formula III:

Formula III

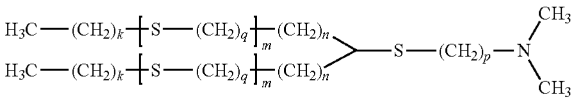

Formula III wherein:

p is 1 to 6;

q are each independently 1 to 8;

n are each independently be 1 to 8;

m are each independently 0 to 8 or 0 to 5; and k are each independently 1 to 8.

9. The compound of claim 8, wherein the m are each independently: 1 to 5; 2 or 3; or 2.

10. The compound of claim 1, wherein the k are each independently 2 to 6.

11. The compound of claim 1, having a structure selected from one of:

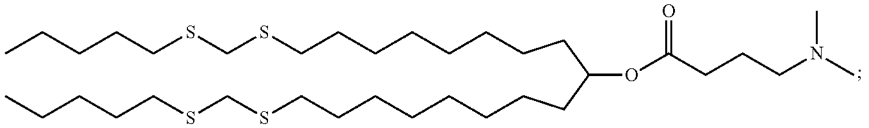

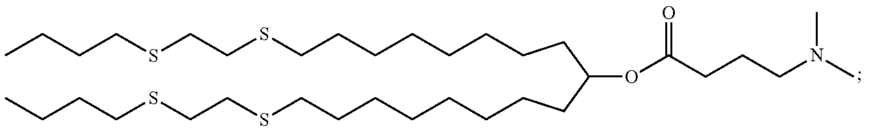

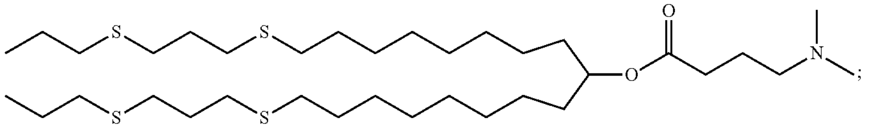

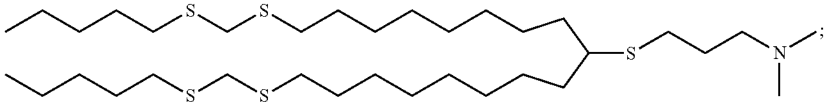

and

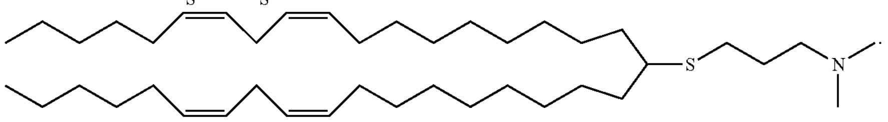

12. A pharmaceutical composition, the pharmaceutical composition comprising the compound of claim 1 and a pharmaceutically acceptable carrier.

13. A lipid nanoparticle composition, the lipid nanoparticle composition comprising the compound of claim 1.

14. The lipid nanoparticle composition of claim 13, the lipid nanoparticle composition comprising a nucleic acid.

15. A pharmaceutical composition, the pharmaceutical composition comprising the compound of claim 5 and a pharmaceutically acceptable carrier.

16. A pharmaceutical composition, the pharmaceutical composition comprising the compound of claim 8 and a pharmaceutically acceptable carrier.

17. A pharmaceutical composition, the pharmaceutical composition comprising the compound of claim 11 and a pharmaceutically acceptable carrier.

18. A lipid nanoparticle composition, the lipid nanoparticle composition comprising the compound of claim 5.

19. A lipid nanoparticle composition, the lipid nanoparticle composition comprising the compound of claim 8.

20. A lipid nanoparticle composition, the lipid nanoparticle composition comprising the compound of claim 11.

* * * * *